US010337071B2

(12) United States Patent
Shibata et al.

(10) Patent No.: US 10,337,071 B2
(45) Date of Patent: Jul. 2, 2019

(54) ONCOGENE NRF2

(75) Inventors: Tatsuhiro Shibata, Tokyo (JP); Shigeru Saito, Tokyo (JP)

(73) Assignees: National Cancer Center, Tokyo (JP); INFOCOM CORPORATION, Tokyo (JP)

( * ) Notice: Subject to any disclaimer, the term of this patent is extended or adjusted under 35 U.S.C. 154(b) by 208 days.

(21) Appl. No.: 13/055,697

(22) PCT Filed: Jul. 15, 2009

(86) PCT No.: PCT/JP2009/003335
§ 371 (c)(1),
(2), (4) Date: Jan. 24, 2011

(87) PCT Pub. No.: WO2010/010672
PCT Pub. Date: Jan. 28, 2010

(65) Prior Publication Data
US 2011/0136246 A1   Jun. 9, 2011

(30) Foreign Application Priority Data

Jul. 25, 2008   (JP) ................................. 2008-192876

(51) Int. Cl.
G01N 33/00   (2006.01)
C12Q 1/6886   (2018.01)
C07H 21/00   (2006.01)

(52) U.S. Cl.
CPC ..... *C12Q 1/6886* (2013.01); *C12Q 2600/106* (2013.01); *C12Q 2600/112* (2013.01);
(Continued)

(58) Field of Classification Search
CPC ............ C12Q 1/6886; C12Q 2600/106; C12Q 2600/136; C12Q 2600/112; C12Q 2600/118
(Continued)

(56) References Cited

U.S. PATENT DOCUMENTS

2007/0042418 A1*  2/2007  Yehiely et al. .................... 435/6
2011/0118298 A1*  5/2011  Fritz ................ G01N 33/57492
                                                                    514/291

FOREIGN PATENT DOCUMENTS

EP          0 960 212        5/2007
WO      WO-2004/005458       1/2004
(Continued)

OTHER PUBLICATIONS

Cho et al., Cancer Letters (2008) 260:96-108.
(Continued)

*Primary Examiner* — Rebecca M Fritchman
(74) *Attorney, Agent, or Firm* — Morrison & Foerster LLP

(57) ABSTRACT

The present invention provides a marker which can be used as an indicator for efficacy prediction of an mTOR related anticancer agent or prognostic prediction, and a novel anticancer agent. The present invention provides a method for efficacy evaluation of a cancer drug, and, specifically, a prediction method for the efficacy of an mTOR-related cancer drug by detecting NRF2 abnormality. In addition, the present invention provides a prognostic prediction method for cancer, and, specifically, a prediction method for the prognosis of cancer by detecting NRF2 abnormality. Furthermore, the present invention provides a novel anticancer agent that targets NRF2.

2 Claims, 4 Drawing Sheets
Specification includes a Sequence Listing.

(52) U.S. Cl.
CPC .. *C12Q 2600/118* (2013.01); *C12Q 2600/136* (2013.01); *Y10T 436/143333* (2015.01)

(58) Field of Classification Search
USPC .................. 436/94; 530/389.1; 536/24.5
See application file for complete search history.

(56) References Cited

FOREIGN PATENT DOCUMENTS

| WO | WO-2006/128041 | 11/2006 |
|----|----------------|---------|
| WO | WO-2008/012534 | 1/2008 |
| WO | WO-2008/114262 | 9/2008 |
| WO | WO-2010/054110 | 5/2010 |

OTHER PUBLICATIONS

Database Geneseq, Accession No. AGI11044 (2007).
Database Geneseq, Accession No. ATM63041 (2008).
Ewan, DDT (2005) 10(14):950-951.
Hashimoto et al., European Journal of Cancer (2008) 44:1022-1029.
Huang et al., Molecular Cell (2003) 11:1491-1501.
Katoh et al., Archives of Biochemistry and Biophysics (2005) 433:342-350.
Kobayashi et al., Genes to Cells (2002) 7:807-820.
Lo et al., The EMBO Journal (2006) 25:3605-3517.
Ohta et al., Cancer Res. (2008) 68:1303-1309.
Okouchi et al., Current Neurovascular Research (2006) 3:249-261.
Ramos-Gomez et al., PNAS (2001) 98(6):3410-3415.
Shibata et al., Gastroenterology (2008) 135:1358-1368.
Shibata et al., PNAS (2008) 105(36):13568-13573.
Zhang et al., Molecular Cancer Therapeutics (2004) 3(7):885-893.
Summary of Examining Meeting for Russian Patent Application No. 2011106957, dated Oct. 22, 2012, 6 pages (including English translation).
Communication Pursuant to Article 94(3) EPC, for EP 09 787 901.9, dated Aug. 3, 2011, 7 pages.
Office Action for RU 2011106957, dated May 17, 2012, 8 pages.
Written Opinion for PCT/JP2009/003335, dated Jan. 25, 2011, 10 pages.
Zhang et al., "A strategy for cancer prevention: Stimulation of the Nrf2-ARE signaling pathway," Molecular Cancer Therapeutics (2004) 3(7):885-893.
Examiner's First Report for AU 2009275110, dated Mar. 14, 2012.
Office Action from Russian Patent Application No. 201106957 dated Jan. 5, 2012 (with English language translation).
Final Rejection issued in Korean patent application No. 10-2011-7002962, dated Feb. 21, 2014, 6 pages, (English translation included).
Second Office Action issued in EP 09787901.9, dated Mar. 6, 2014, 6 pages.
Office Action for CA 2,726,691, dated Nov. 19, 2014, 6 pages.
GenBank Accession No. AK314816.1 (May 2008), 3 pages.
Office Action for IN 1271/DELNP/2011, dated Dec. 19, 2014, 3 pages.
Communication pursuant to Article 94(3) EPC for EP 09 787 901.9, dated Mar. 3, 2015, 7 pages.
Office Action (including translation) for KR 10-2011-7002962, dated Jul. 29, 2013, 5 pages.
Communication pursuant to Article 94(3) EPC for EP 09787901.9, dated Sep. 30, 2016, 6 pages.
GENESEQ Database Accession No. ABL44977, retrieved on Apr. 11, 2002, 1 page.
Office Action (translation) for KR 10-2011-7002962, dated Jan. 22, 2013.
Brantley, Jr., et al., "Association of Complement Factor H and LOC387715 Genotype with Response of Exudative Age-Related Macular Degeneration to Intravitreal Bevacizumab", Ophthalmology (2007) 114(12):2168-2173.
The Second Office Action (translation) for CN 200980128885.0, dated Sep. 3, 2013, 7 pages.
The First Office Action (translation) for CN 200980128885.0, dated Dec. 18, 2012.
Office Action issued by Canadian Patent Office in Application No. 2,726,691, dated Oct. 30, 2013, 5 pages.
Office Action for Japanese Patent Application No. 2011-502574, dated Feb. 19, 2013, 7 pages (including English translation).
Office Action for CA 2,726,691, dated Jan. 11, 2016, 3 pages.

* cited by examiner

[Fig. 1]
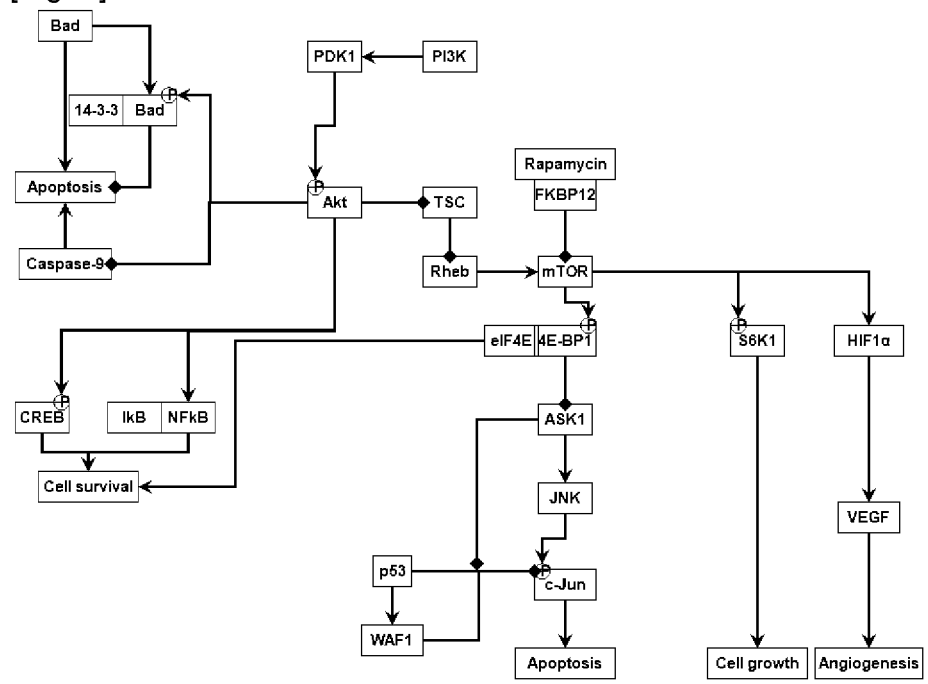
[Fig. 2]
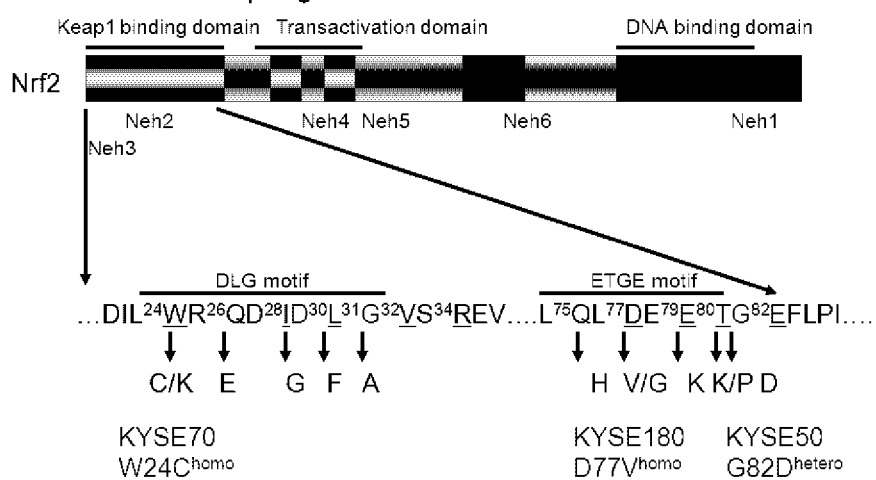

[Fig. 3]
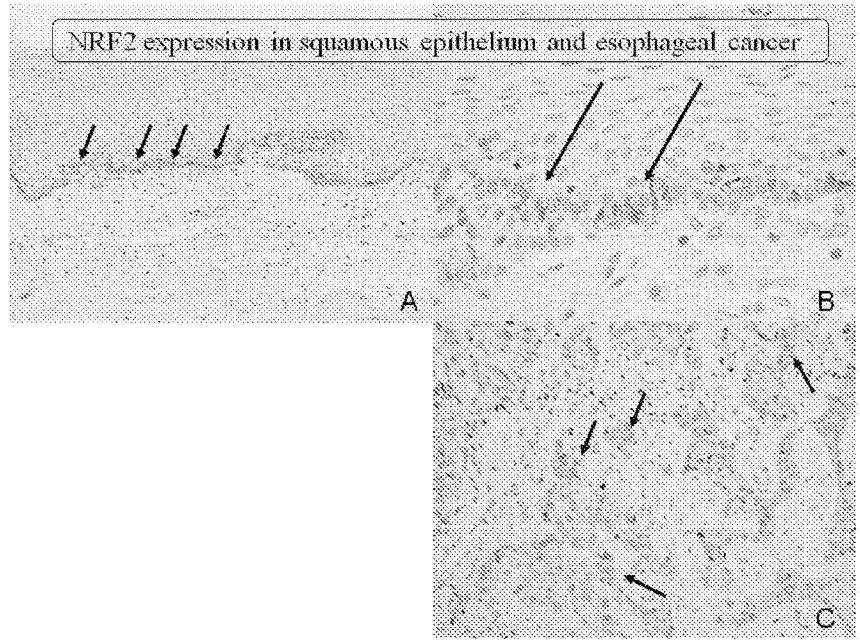
[Fig. 4]
The presence of mutation is significantly associated with poor prognosis in esopahgeal cancers
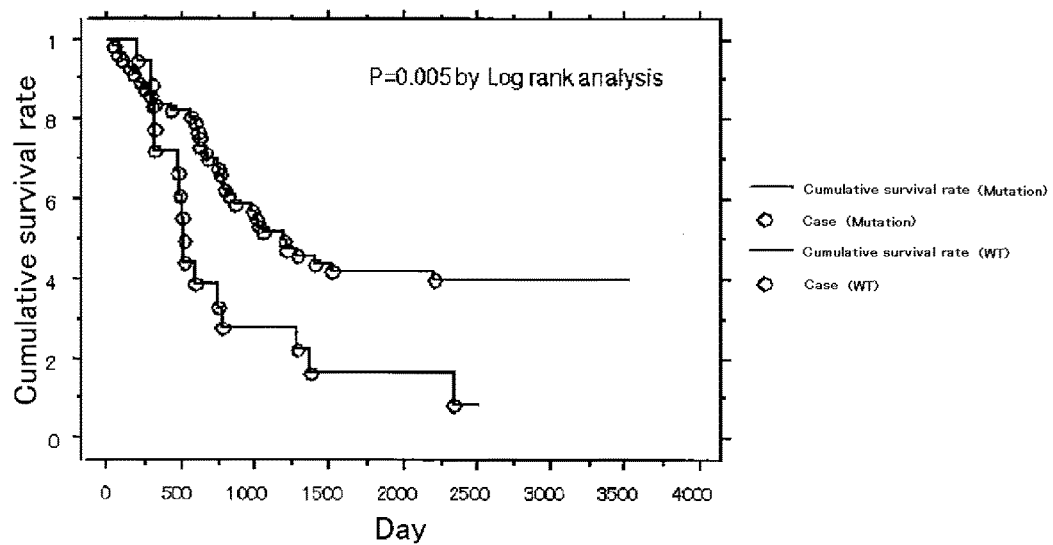

[Fig. 5]
Downregulation of Nrf2 expression by siRNA inhibits proliferation of esophageal cancer cell lines
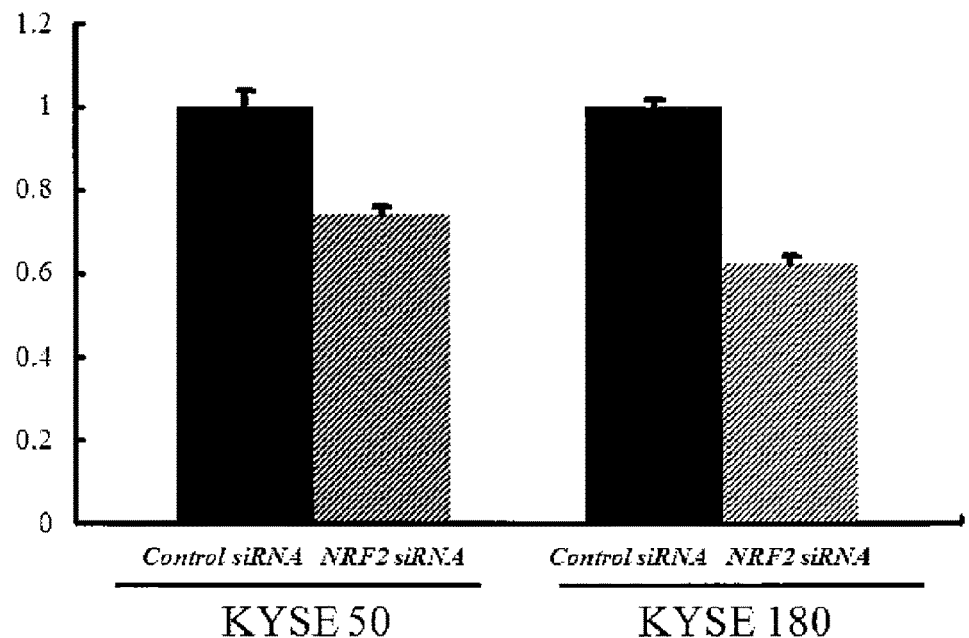
[Fig. 6]
Rapamycin selectively inhibits the proliferation of NRF2-mutated cancer cell lines
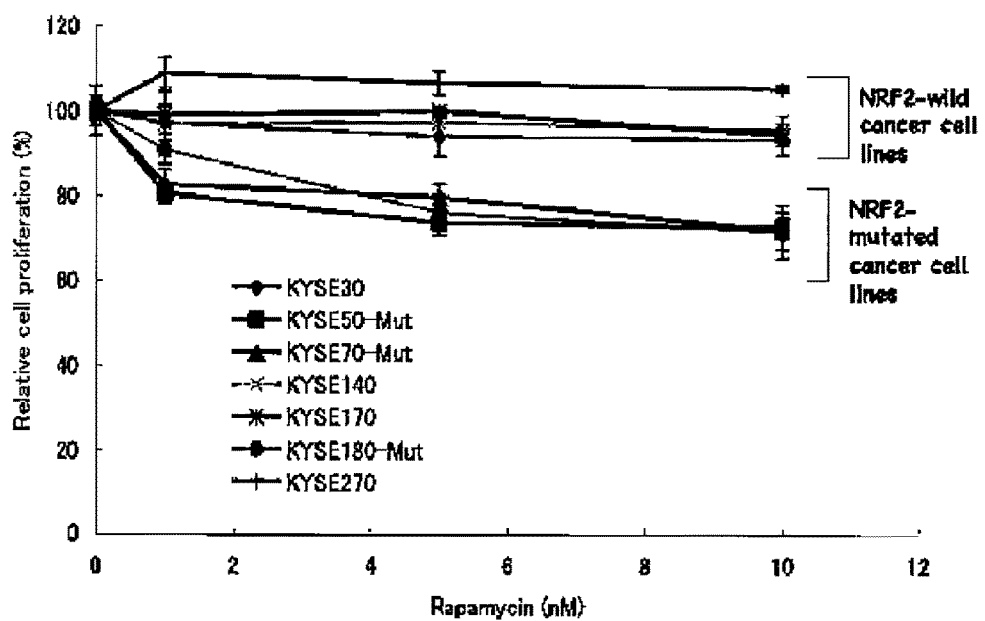

[Fig. 7]
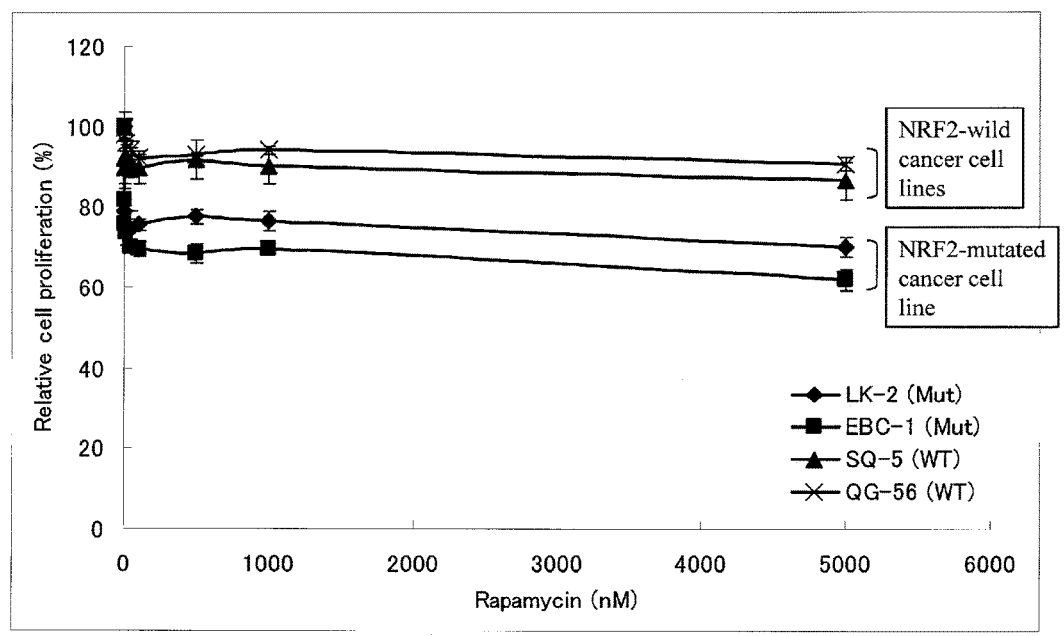
[Fig. 8]
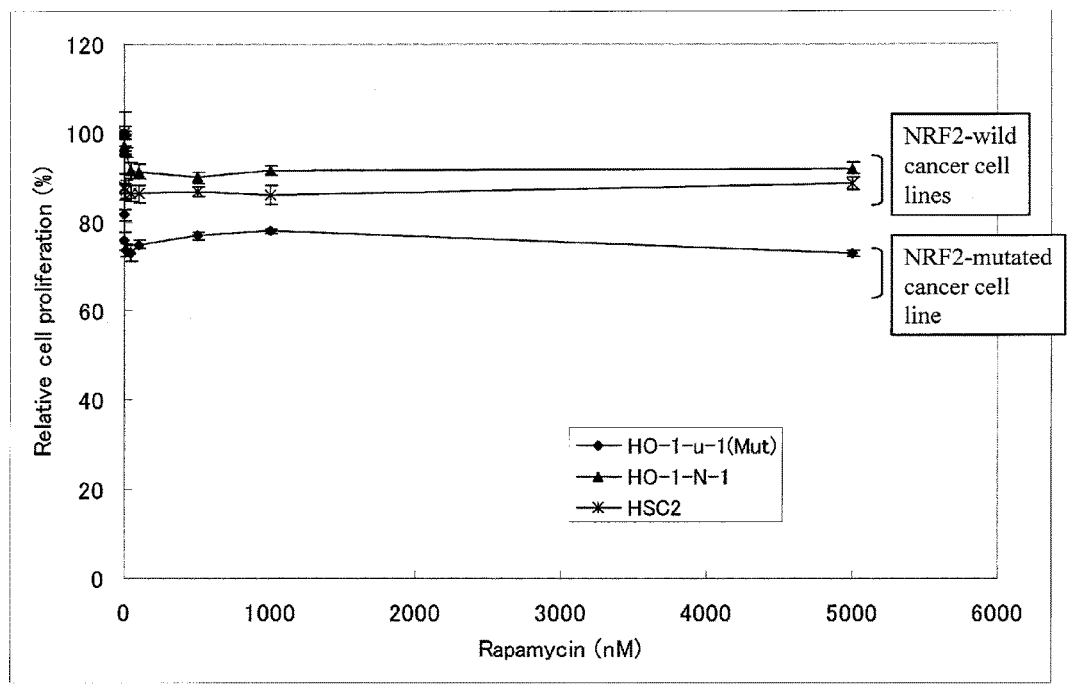

ONCOGENE NRF2

CROSS-REFERENCE TO RELATED APPLICATIONS

This application is the national phase of PCT application PCT/JP2009/003335 having an international filing date of 15 Jul. 2009, which claims benefit of Japanese application No. JP 2008-192876 filed 25 Jul. 2008. The contents of the above patent applications are incorporated by reference herein in their entirety.

REFERENCE TO SEQUENCE LISTING FILED VIA EFS-WEB

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows:

| File Name | Date of Creation | Size (bytes) |
|---|---|---|
| 643102001300seqlist.txt | Jan. 20, 2011 | 11,258 |

TECHNICAL FIELD

The present invention relates to the field of efficacy prediction of a cancer drug, prognostic prediction of cancer, and cancer treatment. More specifically, the present invention relates to an efficacy prediction method for an mTOR-related cancer drug by detecting the abnormalities of NRF2, a prediction method for prognosis of cancer by detecting the abnormalities of NRF2, and a cancer treatment agent that inhibits NRF2 gene or protein.

BACKGROUND ART

It is known that environmental factors, such as smoking, radiation, chronic inflammation caused by virus infection, etc, and exposure to toxic chemical substances influences to onset and development of cancer. Previous researches have revealed that oxidative stress caused by factors which causes abnormalities of DNA and protein is with the development of cancer.

A living organism has the physiological defense mechanism against such oxidative stress. A transcription factor called Nuclear factor erythroid 2-related factor 2 (NRF2) is recognized as one of the important molecules that plays a role in molecular mechanism of said physiological defense system. NRF2 is a DNA binding molecule with high transcriptional induction ability, which is activated when a cell is exposed to oxidative stress, and induces the expression of many groups of enzymes, such as glutathione reductase, which relieve oxidative stress, to protect a cell from the disorder caused by the stress.

For example, NRF2 is known as an important transcription factor that transmits a promoting signal to an antioxidant response element (ARE) component, which is a DNA regulatory element controlling transcription of the gene products which protect cells from carcinogens, oxidants, and other toxic compounds. It has been reported that an enhancer via ARE having cancer inhibitory activity increases the NRF2 level in the nucleus (see Yuesheng et al. Molecular Cancer Therapeutics, 3 (7) 885-893, 2004). In the oral administration model of the benzo-alfa-pyran, it has been appeared that the number of cancers are increased in NRF2 knockout mice compared to in wild type (see Ramos-Gomez et al. Proc. Natl. Acad. Sci. USA, 98, 3410-3415, 2001). In addition, the document suggests that an anticancer agent oltipraz increases the expression of NRF2, and that the anticancer effect of oltipraz is not seen in NRF2 knockout mice, and thus enhancement of NRF2 expression may lead to the anticancer effect.

Furthermore, it has been reported that in a living organism an existence of NRF2 is controlled by negative feedback of Kelch-like ECH-associated protein 1 (KEAP1), and an inhibitor to KEAP1 is under development as an anticancer agent (see Ewan, Drug Discovery Today, 10 (14) 950-951, 2005). Thus, it is expected that drugs targeting NRF2 or KEAP1 which enhance the expression of NRF2 may be used as an anticancer agent.

On the other hand, it is reported that, in lung cancer, constant activation of NRF2 is observed due to the reduced activity of KEAP1 caused by KEAP1 gene mutation is observed and that the activated NRF2, induced constant expression of an anti-oxidant protein. It has been reported that increased expression of NRF2 may be one of the reasons of the resistance of a cancer cells to cisplatin (see Ohta et al. Cancer Res., 68, 1303-1309, 2008 and International Publication WO2006/128041). It has also been reported that administration of alkylating agents such as cisplatin, mephalan, chlorambucil, and BCNU increases the expression of a gene regulated by ARE, such as NRF2. It has been suggested that the increased gene expression products regulated by ARE can be involved in the resistance of cancer cells to the anticancer agents. It has also been suggested that all trans retinoic acid (ATRA), which can bind to NRF2, may be able to enhance the effect of a chemotherapic drug (see International Publication WO2008/012534).

Thus, it is appeared that administration of an alkylating anticancer agent may activate NRF2, and the NRF2 may play a role in resistance to the alkylating anticancer agent. An alkylating anticancer agent interrupts proliferation by cross-linking bases of DNA in a cancer cell. The mechanism of activation of NRF2 upon administration of an alkylating agent remains to be explained. Although a part of mechanism of the acquisition of resistance due to NRF2 against the effect of an alkylating anticancer drug is predicted from a cytoprotective action of NRF2, the overview is not fully understood yet. The relation between anticancer agents other than an alkylating anticancer agent and NRF2 has not been reported.

As noted above, activation of NRF2 observed in a cancer cell has been considered mainly based on the reduced activity of KEAP1 due to KEAP1 gene mutation. The relation between mutation and activation of NRF2 in a cancer cell, and the relation between the NRF2 activation due to the mutation and the malignant alteration of cancer have not been known. Especially, NRF2 has been thought to have an anticancer effect in the onset of the cancer caused by oxidative stress, etc. it has been considered that NRF2 rather suppresses the malignant alteration of cancer. In relation with a chemotherapic drug, it has suggested that NRF2 is responsive to administration of an alkylating agent, and, at least, an all trans retinoic acid enhances the effect of an alkylating agent. However, it has been completely unknown whether an effect of an all trans retinoic acid is based on NRF2 suppressing effect, and if so, what mechanism underlies inhibition. Therefore, the relation between suppression of NRF2 and anticancer agents other than an alkylating anticancer agent has been wholly unknown.

Mammalian target of rapamycin (mTOR) is a serine threonine kinase identified as a target molecule of a macrolide antibiotic, rapamycin and it serves as regulator on cell growth, cell proliferation, cell motility, cell survival, protein synthesis and transcription. Since a rapamycin induces an apoptosis of a cancer cell lacking the function of p53, it is considered that an mTOR inhibitor has an anticancer activity (see Shile Huang et al. Molecular Cell, 11, 1491-1501, 2003). In addition, mTOR inhibitors have been under development as anticancer agent for, for example, renal cancer and pancreatic duct cancer.

An mTOR is also known as an insulin receptor tyrosine kinase. A research on the apoptosis of cerebrovascular endothelial cells in a hyperglycemia patient concludes that an mTOR inhibitor impairs expression of insulin-inducible NRF2-mediated Glutamate-L-cystein ligase-catalytic subunit (GCLc), oxidation reduction balance, and survival of a human cerebrovascular endothelial cell (see Okouchi, Masahiro et al. Current Neurovascular Research, 3 (4) 249-261, 2006). However, especially as for the field of cancer treatment, the effect of the expression of NRF2 on an action of an mTOR inhibitor has not been reported yet.

SUMMARY OF INVENTION

The present invention is directed to a method for predicting cancer by detecting NRF2 gene mutation. Especially the present invention is directed to a method for predicting efficacy of an mTOR-related cancer drug, a method for selecting a efficacious patient by detecting NRF2 gene mutation, or a method for predicting a prognosis of cancer. The present invention also is directed to a method for treating cancer by inhibiting NRF2 gene or NRF2 protein, or a cancer treatment agent that uses NRF2 gene or NRF2 protein inhibitor as an active ingredient.

In a specific embodiment, the present invention is directed to a method for providing information about a selection method for efficacy prediction of an mTOR-related cancer drug or a method for selecting a efficacious patient by detecting NRF2 gene mutation or protein. In addition, the present invention is directed to a method for predicting the effectiveness of an mTOR-related cancer drug or for selecting an efficacious patient by detecting NRF2 gene or protein mutation. Specifically, the present invention is directed to a method for predicting that an mTOR-related cancer drug is effective when NRF2 gene or protein has mutation. The present invention also is directed to a kit that is able to detect a mutation in NRF2 for predicting the effectiveness of an mTOR-related cancer drug. For example, the present invention is directed to kit comprising an nucleic acid capable of binding to the NRF2 gene or a substance capable of binding to the NRF2 protein, (e.g. antibody), wherein the nucleic acid and the substance are capable of detecting a mutation in NRF2. Alternatively, the present invention is directed to a kit which can detect alteration in function of NRF2 due to mutation. For example, a kit which detects digestion of NRF2 by KEAP1 is also is directed to in the present invention.

In another embodiment, the present invention is directed to a method for providing information on a malignancy of cancer or on a prognostic quality by detecting the mutation of NRF2 in a cancer tissue cell from a cancer patient. Alternatively, the present invention is directed to a method for diagnosing malignancy of cancer or for predicting prognosis of cancer which comprises detecting a mutation in NRF2 in a cancer tissue cell from a cancer patient and diagnosing a patient who has a mutation in NRF2 is malignant or predicting a patient who has a mutation in NRF2 is poor prognosis. Alternatively, the present invention is directed to a kit for diagnosing cancer or predicting a prognosis which is able to detect a mutation in NRF2. For example, the present invention is directed to a kit comprising an nucleic acid capable of binding to the NRF2 gene or a substance capable of binding to the NRF2 protein, such as an antibody, wherein the nucleic acid and the substance are able to detect a mutation in NRF2. In addition, the present invention is directed to a kit which is able to detect a mutation by using a gene amplification technology, such as PCR. Furthermore, the present invention is directed to a kit comprising an invader probe, an allele probe, triplex-specific DNase, and a universal fluorescent-labeled probe with a quenching probe, for example, the Invader™ assay kit, etc. In addition, the present invention contains a kit that is able to measure the metergasia of NRF2 caused by mutation. For example, the present invention also is directed to a kit which can detects digestion of NRF2 by KEAP1.

In another embodiment, the present invention is directed to a method for treating cancer comprising inhibiting NRF2 gene or NRF2 protein. The present invention includes a method for treating cancer comprising suppressing NRF2 gene expression. In addition, the present invention is directed to a method for treating cancer comprising suppressing expression or activity of NRF2 protein. Moreover, the present invention is directed to a cancer drug containing an inhibitor of NRF2 gene or NRF2 protein. Specifically, the present invention is directed to an agent for treating cancer which comprises an antisense, dsRNA, a ribozyme, an aptamer for NRF2, a fragment of a NRF2 binding protein, or an antibody or fragment thereof as an active ingredient.

More specifically, the present invention is directed to the following inventions.

(1) A method for obtaining information for predicting response of a cancer patient to an mTOR-related cancer drug, comprising:

(a) detecting DNA or RNA coding mutated NRF2 or mutated NRF2 protein in a sample originated from the patient; and (b) associating the measured level of DNA or RNA coding mutated NRF2 or mutated NRF2 protein with the response of the cancer of the patient to the mTOR-related cancer drug.

(2) A method for obtaining information for predicting response of a cancer of a patient to an mTOR-related cancer drug from a tumor sample originated from the patient, comprising:

(a) detecting DNA or RNA coding mutated NRF2 or mutated NRF2 protein in a sample originated from the patient;

(b) classifying into one of cancer response classes according to the detected level of DNA or RNA coding mutated NRF2 or mutated NRF2 protein, wherein the classification result depends on the expression level of mutated NRF2 gene or mutated NRF2 protein; and (c) predicting response of the cancer of the patient to a cancer drug, based on a known property specific to cancers which belong to the one of the cancer response classes classified.

(3) The method according to (2), wherein high level of DNA or RNA coding mutated NRF2 or mutated NRF2 protein indicates that the patient is highly responsive to an mTOR-related cancer drug.

(4) A kit for predicting a response of cancer patient to an mTOR-related cancer drug, comprising at least one of the substances selected from (i) to (iv):

(i) a substance that binds to DNA or RNA coding NRF2 and does not bind to DNA or RNA coding mutated NRF2;

(ii) a substance that does not bind to NRF2 gene and binds to mutated NRF2 gene;

(iii) a substance that binds to NRF2 protein and does not bind to mutated NRF2 protein; and (iv) a substance that does not bind to NRF2 protein and binds to mutated NRF2 protein.

(5) A method for obtaining information for predicting prognosis of a cancer patient comprising:

(a) detecting DNA or RNA coding mutated NRF2 or mutated NRF2 protein in a sample that is originated from the patient; and (b) associating measured level of DNA or RNA coding mutated NRF2 or mutated NRF2 protein with prognosis of the patient.

(6) The method according to (5), wherein high level of DNA or RNA coding mutated NRF2 or mutated NRF2 protein indicates poor prognosis of the patient.

(7) A cancer drug containing an NRF2 inhibitor as an active ingredient.

(8) The cancer drug according to (6), wherein the NFR2 inhibitor is an antisense, dsRNA, a ribozyme, an aptamer, an NRF2 binding-protein fragment, or an antibody or fragment thereof.

An efficacy prediction method of the present invention is able to predict response of a cancer patient to an mTOR-related cancer drug or to predict whether an mTOR-related cancer drug achieve an effect to the cancer patient before administration. Therefore, the present invention enables to choose a drug expected to be effective for a cancer patient and to avoid unnecessary cancer drug administration to a patient who is not expected to effectively respond, hence, to relieve the patient from pain of unnecessary side effects. The present invention is able to provide information for selecting a cancer drug. In addition, the present invention can provide meaningful information for deciding a therapy regimen strategy for a cancer patient by predicting prognosis of the cancer patient. Furthermore, the method of the present invention for inhibiting NRF2 gene or NRF2 protein or a treatment drug of the present invention comprising an NRF2 gene or NRF2 protein inhibitor can be used as a novel treatment method or a novel treatment drug for cancer.

BRIEF DESCRIPTION OF DRAWINGS

FIG. 1 shows biological pathway related to mTOR.

FIG. 2 shows the positions of the mutations and amino acid substitutions caused thereby in the NRF2 gene in a clinical sample of esophageal cancer and esophageal cancer cell lines (KYSE-50, KYSE-70, KYSE-180).

FIG. 3 shows the result of detection of NRF2 expression in normal esophagus (A and B) and esophageal cancer (C) by immunohistochemical staining using antibody against NRF2. In the figure, an arrow represents a cell expressing NRF2. FIG. 3B is an enlarged view of a part of FIG. 3A.

FIG. 4 shows the result of a statistical analysis (Kaplan-Meier analysis) on relationship between postoperative survival time and presence or absence of gene mutation for esophageal cancer cases screened by NRF2 gene mutation. In the figure, the vertical axis represents a cumulative survival rate, and the horizontal axis represents the elapsed days after surgery.

FIG. 5 shows changes in cell proliferation upon administration or non-administration of dsRNA to the esophageal cancer cell lines that have NRF2 gene mutation (KYSE-50 and KYSE-180). In the figure, the vertical axis is the ratio number of cells administered NRF2 dsRNA to number of cells administered control dsRNA.

FIG. 6 shows changes in proliferation due to rapamycin treatments to the esophageal cancer cell lines without abnormalities in NRF2 gene (KYSE-30, KYSE-140, KYSE-170, KYSE-270) and to the cancer cell lines with abnormalities in NRF2 gene (KYSE-50, KYSE-70, KYSE-180). In the figure, the vertical axis shows a ratio of number of cells of each cell line, when number of cells with 0 nM rapamycin (without drug) is set as 100%. In the figure, horizontal axis shows dosage of rapamycin.

FIG. 7 shows changes in proliferation due to rapamycin treatments to the lung cancer cell lines without abnormalities in NRF2 gene (SQ-5, QG-56) and to the cancer cell lines with abnormalities in NRF2 gene (LK-2, EBC-1). In the figure, the vertical axis shows a ratio of number of cells of each cell line, when number of cells with 0 nM rapamycin (without drug) is set as 100%. In the figure, horizontal axis shows dosage of rapamycin.

FIG. 8 shows changes in proliferation due to rapamycin treatments to the head and neck cancer cell lines without abnormalities in NRF2 gene (HO-1-N-1, HSC2) and to the cancer cell lines with abnormalities in NRF2 gene (HO-1-u-1). In the figure, the vertical axis shows a ratio of number of cells of each cell line, when number of cells with 0 nM rapamycin (without drug) is set as 100%. In the figure, horizontal axis shows dosage of rapamycin.

BEST MODE FOR CARRYING OUT THE INVENTION

A. Prediction of mTOR-related Cancer Drug

In one aspect, the present invention relates to a method or a kit for predicting response of cancer patient to an mTOR-related cancer drug, or a method for obtaining information for predicting response of cancer patient to an mTOR-related cancer drug.

As used herein, "mTOR-related cancer drug" is not limited as long as an agent inhibits expression or activity of an mTOR or a substance that is involved in upstream or downstream pathway of mTOR and is effective for cancer treatment. An mTOR-related cancer drug, includes an agent that directly inhibits an mTOR (mTOR inhibitor), for example, a chemotherapic drug such as sirolimus (also known as rapamycin), everolimus, temsirolimus and deferolimus; protein such as an antibody; peptides such as an antibody fragment; and nucleic acid such as an aptamer, an antisense, and dsRNA. Since an NRF2 inhibitor inhibits mTOR pathway, NRF2 inhibitor of the present invention may also be included as an mTOR inhibitor. It is known that an mTOR pathway is involved in a plurality of pathways as shown in FIG. 1. However, particularly preferable agents that is involved in an mTOR pathway and targeted by an mTOR-related cancer drug in the present application are, for example, type I phosphoinositide 3-kinase (hereinafter, abbreviated as "PI3K"), pyruvate dehydrogenase kinase 1 (hereinafter abbreviated as "PDK1"), FK506 binding protein (FKBP12), Akt (also known as protein kinase B (PKB)), p70 ribosomal protein S6 kinase 1 (hereinafter, abbreviated as "S6K1"), c-Jun N-terminal kinase (hereinafter, abbreviated as "JNK"), and hypoxic inducible factor 1 alfa (hereinafter, abbreviated as "HIF1 alfa"). Therefore, PI3K inhibitors such as TG100115, TCN-P, LY294002, wortmannin, BFZ235, and SF1126; PDK1 inhibitors such as UCN-01, BX912, B-3012, and OSU030313; FKBP12 inhibitors such as AP1903 and tacrolimus; Akt inhibitors such as XL418, LY294002, wortmannin, TCN-P, BV-1701-1, FPA-124, KP372-1, and GSK690693; S6K1 inhibitors such as XL418 and H-89; JNK inhibitors such as AM111, SP600125, a compound described in U.S. Pat. No. 7,199,124, and AS601245; and HIF1 alfa inhibitors such as PX478 and SF1126, are also included in the mTOR-related cancer drug in the present application.

As used herein, "response to an mTOR-related cancer drug" means an effect to at least one of indicators representing condition of a cancer patient when the cancer patient is administered with the mTOR-related cancer drug, wherein the effect is caused by administration of an mTOR-related cancer drug. The indicators include reduction of tumor size, supression of tumor growth, metastasis, prognostic quality, recidivation, or recurrence, etc. As used herein, "good response to an mTOR-related cancer drug" means showing effectiveness of at least one of the indicators indicating the condition of disease in cancer patient a cancer patient who is receiving an mTOR-related cancer drug, compared to not receiving the mTOR-related cancer drug, and includes, for example, reduction of tumor size, repression of tumor growth, repression of metastasis or no metastasis, improvement of prognosis, no recidivation, or no recurrence, etc.

As used herein, "DNA or RNA coding mutated NRF2 gene" is a DNA or RNA coding having mutation(s) in any part of nucleotides or ribonucleotides sequence encoding normal NRF2, for example DNA having mutation(s) in part of sequence of SEQ ID NO.1. As used herein "mutated NRF2 protein" is a protein having mutation(s) in a part of amino acid sequence (SEQ ID NO 2) constituting normal NRF2. Particularly, DNA or RNA coding mutated NRF2 or mutated NRF2 protein is DNA or RNA coding mutated NRF2 or protein that enhances expression level of NRF2 protein by the mutation. In a more particular aspect, the mutated NRF2 protein includes protein in which tryptophan at a position 24 of NRF2 protein is substituted with cysteine or lysine, glutamine at a position 26 of NRF2 protein is substituted with glutamic acid, isoleucine at a position 28 of NRF2 protein is substituted with glycine, leucine at a position 30 of NRF2 protein is substituted with phenylalanine, glycine at a position 31 of NRF2 protein is substituted with alanine, glutamine at a position 75 of NRF2 protein is substituted with histidine, aspartic acid at a position 77 of NRF2 protein is substituted with valine or glycine, glutamic acid at a position 79 of NRF2 protein is substituted with lysine, threonine at a position 80 of NRF2 protein is substituted with lysine or proline, and/or glutamic acid at a position 82 of NRF2 protein is substituted with aspartic acid. The mutated NRF2 gene includes a gene that encodes mutated NRF2 protein in which tryptophan at a position 24 of NRF2 protein is substituted with cysteine or lysine, glutamine at a position 26 of NRF2 protein is substituted with glutamic acid, isoleucine at a position 28 of NRF2 protein is substituted with glycine, leucine at a position 30 of NRF2 protein is substituted with phenylalanine, glycine at a position 31 of NRF2 protein is substituted with alanine, glutamine at a position 75 of NRF2 protein is substituted with histidine, aspartic acid at a position 77 of NRF2 protein is substituted with valine or glycine, glutamic acid at a position 79 of NRF2 protein is substituted with lysine, threonine at a position 80 of NRF2 protein is substituted with lysine or proline, and/or glutamic acid at a position 82 of NRF2 protein is substituted with aspartic acid. A level of a DNA or RNA coding mutated NRF refers to a level of a DNA or RNA coding mutated NRF2 measured by a procedure which can detect mutated gene including a level measured by a method using hybridization such as Southern blotting, Northern blotting, and the ASO method, or by a method using PCR such as the PCR-SSCP, the ARMS, and direct gel assay, or a level given as a value calculated by software suitable for each measuring method.

As used herein, a term "to associate with" used with the relationship between measured level of DNA or RNA coding mutated NRF2 or mutated NRF2 protein and response of a patient to an mTOR-related cancer drug in order to determine response of a patient to the mTOR-related cancer drug, means to compare a presence or level of DNA or RNA coding mutated NRF2 or mutated NRF2 protein in a subject with a level of the DNA or RNA coding mutated NRF2 or the mutated NRF2 protein in a patient whose response to the mTOR-related cancer drug was poor or a patient whose response to the mTOR-related cancer drug is known to be poor, or a patient whose response to the mTOR-related cancer drug was not poor or a patient whose response to the mTOR-related cancer drug is predicted to be not poor. The level of DNA or RNA coding mutated NRF2 or mutated NRF2 protein in a patient for comparison may be obtained, for example, based on the disclosure of the present invention, by measuring the level of mutated NRF2 gene or mutated NRF2 protein in a sample originated from a patient whose response to the mTOR-related cancer drug is previously found, or by evaluating in combination with other evaluation method using other indicator for response to mTOR-related cancer drug. A possibility that a patient responds to an mTOR-related cancer drug can be determined by using the level of DNA or RNA coding mutated NRF2 or mutated NRF2 protein. The level of DNA or RNA coding mutated NRF2 or mutated NRF2 protein can be associated with response to an mTOR-related cancer drug by using statistical analysis. Statistical significance is determined by comparing of two or more groups, and determining a confidence interval and/or a p-value (Dowdy and Wearden, Statistics for Research, John Wiely & Sons, NewYork, 1983). A confidence interval of the present invention may be 90%, 95%, 98%, 99%, 99.5%, 99.9%, or 99.99%, for example. In addition, a p value of the present invention may be 0.1, 0.05, 0.025, 0.02, 0.01, 0.005, 0.001, 0.0005, 0.0002, or 0.0001, for example.

Preferably, DNA or RNA coding mutated NRF2 or mutated NRF2 protein can be associated with response of a patient to an mTOR-related cancer drug by presence or absence thereof. For another example, a level of DNA or RNA coding mutated NRF2 or mutated NRF2 protein in a sample originated from a patient may be associated with response of a patient to an mTOR-related cancer drug by comparing with a threshold level established as a response indicator to an mTOR-related cancer drug for DNA or RNA coding mutated NRF2 or mutated NRF2 protein. Such a threshold level may be determined, for example, with sensitivity of not less than 50, 55, 60, 65, 70, 75, 80, 85, 90, 91, 92, 93, 94, 95, 96, 97, than 98%. The threshold level may be determined, for example, with specificity of not less than 40, 45, 50, 55, 60, 65, 70, 75, 80, 85, 90, 91, 92, 93, 94, 95, 96, 97, or 98%.

A determination of response to an mTOR-related cancer drug means predicting the course or the outcome of condition of a patient by administration of mTOR-related cancer drug, and does not mean that the course or outcome of the condition of a patient by administration can be predicted with 100% accuracy. The determination of response to an mTOR-related cancer drug means to determine whether the likelihood of a certain course or outcome increases by administration of the anticancer agent, and it does not mean to determine the likelihood of the certain course or outcome happens by comparing to the case where the course or outcome does not happen. Namely, a result of the determination of response to an mTOR-related cancer drug shows that, by administration of an mTOR-related cancer drug, a specific course or outcome is more likely to be observed in a patient whose level of DNA or RNA coding mutated NRF2 or mutated NRF2 protein is increased, compared with a patient who does not show such feature.

As used herein, a "cancer response class" is a cancer group providing a similar property. More particularly, cancer response class is a cancer group showing a similar expression pattern of a specific gene expression or showing a similar clinical condition. Members who belong to a certain cancer response class show the same or similar response to an mTOR-related cancer drug. The gene expression or the clinical condition of the members belonging to the response class is, preferably, different and distinguishable from gene expression or clinical condition of members not belonging to the same response class. As such gene expression, mutated NRF2 gene expression is preferable. At least two classes, "response to mTOR is high" and "response to mTOR is low", can be included in the cancer response classes. In addition, larger number of classes may be included as well.

As used herein, "classifying into one class among the cancer response classes" means grouping a cancer patient according to the level of DNA or RNA coding mutated NRF2 or NRF2 protein in a sample originated from the patient. The level normally means the amount of the DNA, RNA or protein such as expression level, but may mean the level of mutation such as number or extent of the mutation. The grouping may be done according to an absolute or a relative indicator. For example, the grouping may be carried out by classifying a target patient into a group with a predetermined level of DNA or RNA coding mutated NRF2 or mutated NRF2 protein, according to the level of DNA or RNA coding mutated NRF2 or mutated NRF2 protein of the patient. Alternatively, after determining an level of DNA or RNA coding mutated NRF2 or mutated NRF2 protein in a group of unspecified patients including the target patient, the patients may be classified into two or more groups according to the difference in the relative level of DNA or RNA coding mutated NRF2 or mutated NRF2 protein. In addition, classification may be done using degree of difference compared to the level of DNA or RNA coding mutated NRF2 or mutated NRF2 protein in healthy individuals as an indicator. Preferably, on comparison, a subject is classified into a class with higher response to mTOR when a level of DNA or RNA coding mutated NRF2 or mutated NRF2 protein is higher.

In one embodiment, a method or a kit of the present invention for predicting response of cancer patient to an mTOR-related cancer drug can be carried out based on a known method that uses a nucleic acid molecule, such as Southern hybridization, Northern hybridization, dot hybridization, fluorescence in situ hybridization (FISH), a DNA microarray, the ASO method, etc. may be included in such a method. Using the prediction kit, analysis can be performed qualitatively, quantitatively, or semi-quantitatively.

Specifically, a method of the present invention for predicting response of cancer patient to an mTOR-related cancer drug can be carried out, for example, with the following steps of:

(a) preparing a sample originated from a patient;

(b) contacting the sample with at least one nucleic acid, wherein the nucleic acid is selected from (i) and (ii):

(i) nucleic acid that specifically binds to DNA or RNA coding normal NRF2 and does not bind to DNA or RNA coding mutated NRF2, and nucleic acid that binds to DNA or RNA coding normal NRF2 and DNA or RNA coding mutated NRF2, and (ii) nucleic acid that does not bind to DNA or RNA coding normal NRF2 and specifically bind to DNA or RNA coding mutated NRF2;

(c) detecting binding of the DNA or RNA to the nucleic acid and measuring the level of DNA or RNA coding mutated NRF2; and (d) predicting response of a cancer patient to an mTOR-related cancer drug from the level of DNA or RNA coding mutated NRF2, wherein existence or increase of DNA or RNA coding mutated NRF2 indicates that the patient highly likely responses to the mTOR-related cancer drug.

A kit of the present invention for predicting response of cancer patient to an mTOR-related cancer drug based on a known method that uses a nucleic acid molecule includes nucleic acids that specifically binds to a specific gene (for example, DNA or RNA coding normal NRF2, DNA or RNA coding mutated NRF2, or both). Specifically a kit of the present invention for predicting a response of cancer patient to an mTOR-related cancer drug comprises at least one of the substances selected from (i) to (iv):

(i) a substance that binds to DNA or RNA coding NRF2 and does not bind to DNA or RNA coding mutated NRF2;

(ii) a substance that does not bind to NRF2 gene and binds to mutated NRF2 gene;

(iii) a substance that binds to NRF2 protein and does not bind to mutated NRF2 protein; and (iv) a substance that does not bind to NRF2 protein and binds to mutated NRF2 protein.

The nucleic acid used for the kit can be obtained by chemical synthesis, or by preparing a gene containing desired nucleic acid from a biomaterial and then amplifying it using the primer designed to amplify the desired nucleic acid.

In another embodiment, a method or a kit of the present invention may be based on a known method using PCR. For example, ARMS (Amplification Refractory Mutation System) method, the RT-PCR (Reverse transcriptase-PCR) method, Nested PCR method, etc. may be included in such a method. The amplified nucleic acid, may be detected by using dot blot hybridization method, surface plasmon resonance method (SPR method), PCR-RFLP method, In situ RT-PCR method, PCR-SSO (sequence specific Oligonucleotide) method, PCR-SSP method, the AMPFLP (Amplifiable fragment length polymorphism) method, MVR-PCR method, and the PCR-SSCP (single strand conformation polymorphism) method. Analysis of the kit can be performed qualitatively, quantitatively, or semi-quantitatively.

Specifically, a method of the present invention for predicting response of a cancer patient to an mTOR-related cancer drug can be carried out, for example, with the following steps of:

(a) preparing a sample originated from a patient;

(b) amplifying at least one nucleic acid selected from DNA or RNA coding normal NRF2 and DNA or RNA coding mutated NRF2;

(c) detecting an amplification level of nucleic acid and measuring the level of DNA or RNA coding mutated NRF2; and (d) predicting response of a cancer patient to an mTOR-related cancer drug from the level of DNA or RNA coding mutated NRF2, wherein existence or increase of DNA or RNA coding mutated NRF2 indicates that the patient highly responses to an mTOR-related cancer drug.

A kit of the present invention for predicting response of cancer patient to an mTOR-related cancer based on a known method using PCR includes a primer that specifically binds to a part of specific gene (for example, DNA or RNA coding normal NRF2, DNA or RNA coding mutated NRF2, or both). The primer used in the kit can be prepared by chemical synthesis, properly designed by using method known to those skilled in the art with referring the disclosure of the present specification and known information, and prepared by chemical synthesis.

In the other embodiment, a method of the present invention for predicting response of cancer patient to an mTOR-related cancer drug can be carried out, for example, using a known method as the Invader™ method (see, for example, Kwiatkowski, R. W. et al.: "Clinical genetic, and pharmacogenetic applications of the Invader assay." Mol. Diagn., 4: 353-364, 1999).

For example, the method for predicting response of cancer patient to an mTOR-related cancer drug, according to the present specification, can be carried out, by the following steps of:

(a) preparing a sample originated from a patient;

(b) forming a triplex with DNA which is complementary to allele probe by contacting the samples with nucleic acid as described in the following (i) and (ii):

(i) an allele-specific probe comprising a sequence complementary to a part of DNA coding normal NRF2 and a sequence complementary to a part of quenching probes (flap) and/or a sequence complementary to a part of DNA coding mutated NRF2 and a sequence complementary to a part of quenching probes (flap), and (ii) invader probe comprising a sequence complementary to a part of DNA coding normal NRF2 and/or DNA coding mutated NRF2;

(c) releasing a flap from the nucleic acid formed triplex by contacting triplex-specific DNase to the sample of the nucleic acid obtained from (b);

(d) contacting the released flaps to a universal fluorescent-labeled probe comprising a sequence complementary to the flaps and the quenching probes;

(e) generating fluorescence by releasing the fluorescent-labeled probe by contacting triplex-specific DNase to the sample of the nucleic acid obtained from (d); and (f) measuring the level of DNA coding mutated NRF2 by detecting the generated fluorescence, wherein existence or increase of DNA coding mutated NRF2 indicates that the patient highly likely responses to an mTOR.

In one embodiment, a kit of the present invention for predicting response of cancer patient to an mTOR-related cancer drug may be a kit suitable for the above Invader™ method. For example, the kit of the present invention for predicting response of cancer patient to an mTOR-related cancer drug may comprise an allele-specific probe comprising a sequence complementary to a part of DNA coding normal NRF2 and a sequence complementary to a part of quenching probes (flap) and/or an allele-specific probe comprising a sequence complementary to a part of DNA coding mutated NRF2 and a sequence complementary to a part of quenching probes (flap), an invader probe comprising a sequence complementary to a part of DNA coding normal NRF2 and/or DNA coding mutated NRF2, triplex-specific DNase, and a universal fluorescent-labeled probe provided with a quenching probe. The flaps are preferably different among allele-specific probes. The fluorescent labels may be suitably selected from which is known to those skilled in the art, and preferably are different among universal fluorescent-labeled probes. For example, FAM and VIC can be used as a fluorescent-label.

A probe included in the above kit of present invention for predicting response of cancer patient to an mTOR-related cancer drug can be prepared by chemical synthesis, properly designed by a method known to those skilled in the art with referring the disclosure of the present specification and known information, and prepared by chemical synthesis, or can be prepared by preparing gene containing desired nucleic acid sequences from a biomaterial and amplifying it using the primer designed to amplify the desired nucleic acid sequence. Triplex-specific DNase included in a kit of the present invention is commercially available (for example, Cleavase, Third Wave Japan, inc).

In the other embodiment, a method or a kit of the present invention for predicting response of cancer patient to an mTOR-related cancer drug may be based on a known method that uses an antibody molecule. For example, ELISA (Catty, Raykundalia, 1989), radioimmunoassay (Catty, Murphy, 1989), immunohistochemical methods (Heider et al., 1993), Western blotting, etc. may be included as such a method.

In another embodiment, a method of the present invention for predicting response of cancer patient to an mTOR-related cancer drug can be comprising of:

(a) preparing a sample originated from a patient;

(b) contacting at least one antibody with the sample, wherein the antibody is selected from following (i) and (ii):

(i) antibody that specifically binds to NRF2 protein and does not bind to mutated NRF2 protein, and antibody that binds to NRF2 protein and mutated NRF2 protein, and (ii) antibody that does not bind to NRF2 protein and specifically bind to mutated NRF2 protein;

(c) detecting binding of the protein to the antibody and measuring the expression level of mutated NRF2 protein; and (d) predicting a response of cancer patient to an mTOR-related cancer drug from the expression level of mutated NRF2 protein, wherein expression or increased expression of mutated NRF2 protein indicates that the patient highly likely responses to the mTOR.

A kit of the present invention includes an antibody or fragment thereof that specifically binds to specific protein (for example, NRF2 protein, mutated NRF2 protein, or both). As long as it binds to a target protein, any structure, size, immunoglobulin class, origin, etc. of the antibody or the fragment thereof can be used. The antibody or the fragment thereof included in the kit of the present invention may be monoclonal or polyclonal. A fragment of the antibody is a part of the antibody (partial fragment) or a peptide containing a part of the antibody that retains the binding activity to the antigen of the antibody. The fragment of antibody may include $F(aN)_2$, Fab', Fab, single chain Fv (scFv), disulfide-bonded Fv (dsFv) or a polymer thereof, a dimerized V region (Diabody), or a peptide containing CDR. As used herein, CDR is defined by Kabat et al., "Sequences of Proteins of Immunological Interest", U.S. Department of Health and Human Services, 1983, or Chothia et al., J. Mol. Biol., 196, 901-917, 1987. The kit of the present invention may include isolated nucleic acid encoding the antibody included in the kit of the present invention or encoding an amino acid sequence of fragment of the antibody, a vector including the nucleic acid, and a cell carrying the vector.

An antibody can be obtained by a method which is well known to those skilled in the art. For example, a polypeptide retaining all or a part of the target proteins, or an expression vector for mammalian cells integrating a polynucleotide that encodes them is prepared as an antigen. After immunization of an animal using the antigen, an immune cell obtained from the immunized animal and a myeloma cell are fused to obtain a hybridoma. Then an antibody is collected from the culture of the hybridoma. Finally a monoclonal antibody against NRF2 protein or mutated NRF2 protein can be obtained by performing antigen-specific purification of the obtained antibody using NRF2 protein or mutated NRF2 protein or the part thereof, which was used for the antigen. A polyclonal antibody may be prepared by immunizing an animal with the same antigen as the above, collecting a blood sample from the immunized animal, separating serum from the blood, and then performing antigen specific purification of the serum, using the above-mentioned antigen. A fragment of the antibody can be obtained by treating the obtained antibody with enzyme or by using sequence information of the obtained antibody.

Binding of a label to an antibody or its fragment can be performed by a method generally known in the art. For example, a protein or a peptide may be fluorescent-labeled, by washing the protein or the peptide with a phosphate buffer, adding dye prepared with DMSO, buffer, etc., and then standing for 10 minutes at room temperature after mixing the solution. In addition, a commercially available labeling kit such as, a biotin labeling kit such as Biotin Labeling Kit-NH2, Biotin Labeling Kit-SH (Dojindo Laboratories); an alkaline phosphatase labeling kit such as Alkaline Phosphatase Labeling Kit-NH2, Alkaline Phosphatase Labeling Kit-SH (Dojindo Laboratories); a peroxidase labeling kit such as Peroxidase Labeling Kit-NH2, Peroxidase Labeling Kit-NH2 (Dojindo Laboratories); a phycobiliprotein labeling kit such as Allophycocyanin Labeling Kit-NH2, Allophycocyanin Labeling Kit-SH, B-Phycoerythrin Labeling Kit-NH2, B-Phycoerythrin Labeling Kit-SH, R-Phycoerythrin Labeling Kit-NH2, R-Phycoerythrin Labeling Kit-SH (Dojindo Laboratories); a fluorescent labeling kit such as Fluorescein Labeling Kit-NH2 HiLyte Fluor™ 555 Labeling Kit-NH2, HiLyte Fluor™ 647 Labeling Kit-NH2 (Dojindo Laboratories); and DyLight 547 and DyLight 647 (Techno Chemical Corp.), Zenon™, Alexa Fluor™ antibody labeling kit, Qdot™ antibody labeling kit (Invitrogen Corporation) and EZ-Label Protein Labeling Kit (Funakoshi Corporation) may be used for labeling. The labeled antibody or its fragment can be detected by using an adequate instrument for proper labeling.

As a sample for a prediction method and a prediction kit, according to the present specification, tissue sample or fluid that is obtained from a subject for a biopsy can be used, for example. The sample is not particularly limited as long as it is adequate for immunological determination of the present invention; for example, it may be included tissue, blood, plasma, serum, lymph fluid, urine, serous fluid, spinal fluid, synovial fluid, aqueous humor, lacrimal fluid, saliva, or their fraction or treated material. Preferably tissue, especially cancer tissue, is used as a sample. For a method of the present invention for predicting response of cancer patient to an mTOR-related cancer drug, a cancer type of interest is not particularly limited, and preferably is a solid cancer, such as lung cancer, head and neck cancer, esophageal cancer, cervical cancer, biliary cancer, breast cancer, and malignant melanoma. Analysis of the kit can be performed qualitatively, quantitatively, or semi-quantitatively.

B. Prognosis of Cancer

In the other aspect, the present invention is a method or kit for predicting a prognosis of cancer patient, or a method for obtaining information for predicting a prognosis of cancer patient. In the present invention, the prognostic prediction may be determining a risk of recurrence, metastasis or especially death of the patient as an outcome of cancer.

As used herein, "prognosis" means a course or an outcome of a cancer patient after inhibition or mitigation of tumor growth by surgical treatment, etc (for example, presence or absence of metastasis, vital status, etc.). In the present specification, prognosis may be a vital status at the time of 1, 2, 3, 4, 5, 6, 7, 8, 9, 10, 15, 20 years or more after the inhibition or mitigation of tumor growth by surgical treatment. A prognosis may be predicted by examining a biomarker, mutated NRF2 protein or gene coding the mutated NRF2 protein. Prognostic prediction can be made by determining whether prognosis of a patient is good or poor or determining probability of good prognosis or poor prognosis by presence or absence, or increase or decrease of the biomarker. As used herein, "prognostic determination" and "prognostic evaluation" is used synonymously with "prognostic prediction".

As used herein, "good prognosis" means that a condition of a patient has not been critical for a long period of time (for example, 3, 5, 6, 7, 8, 9, 10, 15, 20 years or more) after the inhibition or mitigation of tumor growth by surgical treatment for patients, etc. Alternatively, good prognosis may mean survival, non-metastasis, non-recurrence, or non-recidivation for such a long period. For example, good prognosis may mean surviving, preferably without metastasis or recurrence, for at least three years or especially at least five years. The most preferable status for good prognosis is long-term disease-free survival. "Good prognosis" as used herein may also include any state, wherein diseases such as metastasis may be found but low-grade malignancy and not seriously affect survivability.

As used herein, "poor prognosis" means that a condition of a patient becomes fatal in a short period of time (for example, 1, 2, 3, 4, 5 year(s) or less) after the inhibition or mitigation of tumor growth by surgical treatment, etc. Alternatively poor prognosis may mean that death, metastasis, recurrence, or recidivation in such a short period. For example, poor prognosis may mean recurring, metastasis, or death within at least three years or especially at least five years.

As used herein, a term "to associate with" used with the relationship between measured expression level of DNA or RNA coding mutated NRF2 or mutated NRF2 protein and response of a patient in order to determine response of a patient, means to compare a presence or level of DNA or RNA coding mutated NRF2 or mutated NRF2 protein in a subject with an level of the DNA or RNA coding mutated NRF2 or the mutated NRF2 protein in a patient whose response was poor or a patient whose response is known to be poor, or a patient whose response was not poor or a patient whose response is predicted to be not poor. Also, "to associate with" is used comparing a presence or level of DNA or RNA coding mutated NRF2 or mutated NRF2 protein in a subject with a level of the DNA or RNA coding mutated NRF2 or the mutated NRF2 protein in a healthy subject who is not developed cancer. The level of DNA or RNA coding mutated NRF2 or mutated NRF2 protein in a patient for comparison may be obtained, for example, based on the disclosure of the present invention, by measuring the level of DNA or RNA coding mutated NRF2 or mutated NRF2 protein in a sample originated from a patient whose response is previously found, or by evaluating in combination with other evaluation method using other response indicator. The level of DNA or RNA coding mutated NRF2 or mutated NRF2 protein can be used to predict possible death, recurrence or metastasis for the patient. A prognostic factor can be associated with prognosis by using statistical analysis. Statistical significance is determined by comparing of two or more groups, and determining a confidence interval and/or a p-value (Dowdy and Wearden, Statistics for Research, John Wiely & Sons, NewYord, 1983). A confidence interval of the present invention may be 90%, 95%, 98%, 99%, 99.5%, 99.9%, or 99.99%, for example. In addition, a p value of the present invention may be 0.1, 0.05, 0.025, 0.02, 0.01, 0.005, 0.001, 0.0005, 0.0002, or 0.0001, for example.

For example, DNA or RNA coding mutated NRF2 or mutated NRF2 protein of the present invention can be associated with response of a patient by presence or absence thereof. For another example, a level of a DNA or RNA coding mutated NRF2 or mutated NRF2 protein in a sample originated from a patient may be associated with response of a patient by comparing with a threshold level established as a prognosis indicator for DNA or RNA coding mutated NRF2 or mutated NRF2 protein of the present invention. Such a threshold level may be determined, for example, with sensitivity of not less than 50, 55, 60, 65, 70, 75, 80, 85, 90, 91, 92, 93, 94, 95, 96, 97, or 98%. The threshold level may be determined, for example, with specificity of not less than 40, 45, 50, 55, 60, 65, 70, 75, 80, 85, 90, 91, 92, 93, 94, 95, 96, 97, or 98%.

A prognostic determination means predicting the course or the outcome of condition of a patient, and does not mean that the course or outcome of the condition of a patient can be predicted with 100% accuracy. The prognostic determination means to determine whether the likelihood of a certain course or outcome increases, and it does not mean to determine the likelihood of the certain course or outcome happens by comparing to the case where the course or outcome does not happen. Namely, a prognostic determination result shows that a specific course or outcome is more likely to be observed in a patient whose level of mutated NRF2 gene or mutated NRF2 protein of the present invention is increased or decreased, compared with a patient who does not show such feature.

In one embodiment, a method or a kit of the present invention for predicting prognosis of cancer patient can be based on a known method that uses a nucleic acid molecule. For example, Southern hybridization, Northern hybridization, dot hybridization, fluorescence in situ hybridization (FISH), a DNA microarray, etc. may be included as such a method. As a sample of the kit, tissue sample or fluid obtained from a subject for a biopsy can be used, for example. The sample is not particularly limited as long as it is adequate for immunological determination of the present invention, and may include tissue, blood, plasma, serum, lymph fluid, urine, serous fluid, spinal fluid, synovial fluid, aqueous humor, lacrimal fluid, saliva, or their fraction or treated sample. Preferably, sample for the kit is tissue, especially cancer tissue. Analysis can be performed qualitatively, quantitatively, or semi-quantitatively.

A method of the present invention for predicting prognosis of cancer patient can be carried out, for example, with the following steps of:

(a) preparing a sample originated from the patient;

(b) contacting at least one nucleic acid with the sample, wherein the nucleic acid is selected from (i) and (ii):

(i) nucleic acid that specifically binds to DNA or RNA coding normal NRF2 and does not bind to DNA or RNA coding mutated NRF2, and nucleic acid that binds to DNA or RNA coding normal NRF2 and DNA or RNA coding mutated NRF2, and (ii) nucleic acid that does not bind to DNA or RNA coding normal NRF2 and specifically bind to DNA or RNA coding mutated NRF2e;

(c) detecting binding of the nucleic acid to the DNA or RNA and measuring the level of DNA or RNA coding mutated NRF2; and (d) predicting a prognosis of cancer patient from the expression level of DNA or RNA coding mutated NRF2, wherein expression or increased expression of DNA or RNA coding mutated NRF2 indicates poor prognosis of the cancer patient.

A kit of the present invention for predicting prognosis of cancer patient includes nucleic acid that specifically binds to a specific DNA or RNA (for example, DNA or RNA coding normal NRF2, DNA or RNA coding mutated NRF2, or both). Specifically a kit of the present invention for predicting prognosis of cancer patient comprises at least one of the substances selected from (i) to (iv):

(i) a substance that binds to DNA or RNA coding NRF2 and does not bind to DNA or RNA coding mutated NRF2;

(ii) a substance that does not bind to NRF2 gene and binds to mutated NRF2 gene;

(iii) a substance that binds to NRF2 protein and does not bind to mutated NRF2 protein; and (iv) a substance that does not bind to NRF2 protein and binds to mutated NRF2 protein.

The nucleic acid used for the kit can be obtained by chemical synthesis or by preparing a gene containing desired nucleic acid sequence from a biomaterial, and amplifying it using the primer designed to amplify the desired nucleic acid sequence.

In the other embodiment, a method of the present invention for predicting prognosis of cancer patient can be carried out, for example, using a known method as the Invader™ method (see, for example, Kwiatkowski, R. W. et al.: "Clinical genetic, and pharmacogenetic applications of the Invader assay." Mol. Diagn., 4: 353-364, 1999). For example, the method for predicting prognosis of cancer patient can be carried out, by the following steps of:

(a) preparing a sample originated from a patient;

(b) forming a triplex with DNA which is complementary to allele probe by contacting the samples with nucleic acid as described in the following (i) and (ii):

(i) an allele-specific probe comprising a sequence complementary to a part of DNA coding normal NRF2 and a sequence complementary to a part of quenching probes (flap) and/or a sequence complementary to a part of DNA coding mutated NRF2 and a sequence complementary to a part of quenching probes (flap), and (ii) invader probe comprising a sequence complementary to a part of DNA coding normal NRF2 and/or DNA coding mutated NRF2;

(c) releasing a flap from the nucleic acid formed triplex by contacting triplex-specific DNase to the sample of the nucleic acid obtained from (b);

(d) contacting the released flaps to a universal fluorescent-labeled probe comprising a sequence complementary to the flaps and the quenching probes;

(e) generating fluorescence by releasing the fluorescent-labeled probe by contacting triplex-specific DNase to the sample of the nucleic acid obtained from (d); and (f) measuring the level of DNA coding mutated NRF2 by detecting the generated fluorescence, wherein existence or increase of DNA coding mutated NRF2 indicates poor prognosis of the cancer patient.

In one embodiment, a kit of the present invention for predicting prognosis of cancer patient may be a kit suitable for the above Invader™ method. For example, the kit of the present invention for predicting prognosis of cancer patient may comprise an allele-specific probe comprising a sequence complementary to a part of DNA coding normal NRF2 and a sequence complementary to a part of quenching probes (flap) and/or an allele-specific probe comprising a sequence complementary to a part of DNA coding mutated NRF2 and a sequence complementary to a part of quenching probes (flap), an invader probe comprising a sequence complementary to a part of DNA coding normal NRF2 and/or DNA coding mutated NRF2, triplex-specific DNase, and a universal fluorescent-labeled probe provided with a quenching probe. The flaps are preferably different among allele-specific probes. The fluorescent labels may be suitably selected from which is known to those skilled in the art, and preferably are different among universal fluorescent-labeled probes. For example, FAM and VIC can be used as a fluorescent-label.

A probe included in a kit of present invention for predicting prognosis of cancer patient can be prepared by chemical synthesis, properly designed by a method known to those skilled in the art with referring the disclosure of the present specification and known information, and prepared by chemical synthesis, or can be prepared by preparing gene containing desired nucleic acid sequences from a biomaterial and amplifying it using the primer designed to amplify the desired nucleic acid sequence. Triplex-specific DNase included in a kit of the present invention is commercially available (for example, Cleavase, Third Wave Japan, inc).

In another embodiment, a method or a kit of the present invention for predicting prognosis of cancer patient may be based on a known method that uses an antibody molecule. For example, ELISA (Catty, Raykundalia, 1989), radioimmunoassay (Catty, Murphy, 1989), immunohistochemical methods (Heider et al., 1993), Western blotting, etc. may be included as such a method.

A method of the present invention for predicting prognosis of cancer patient can be carried out, for example, with the following steps of:

(a) preparing a sample originated from the patient;

(b) contacting at least one antibody with the sample, wherein the antibody is selected from (i) and (ii):

(i) antibody that specifically binds to NRF2 protein and does not bind to mutated NRF2 protein, and antibody that binds to NRF2 protein and mutated NRF2 protein, (ii) antibody that does not bind to NRF2 protein and specifically bind to mutated NRF2 protein;

(c) detecting binding of the protein to the antibody and measuring the expression level of mutated NRF2 protein; and (d) predicting a prognosis of cancer patient from the expression level of mutated NRF2 protein, wherein expression or increased expression of mutated NRF2 protein indicates poor prognosis of cancer patient.

A kit of the present invention for predicting prognosis of cancer patient includes an antibody or fragment thereof that binds to specific protein (for example, NRF2 protein, mutated NRF2 protein or both). As long as it binds to a target protein, any structure, size, an immunoglobulin class, origin, etc. of the antibody or fragment thereof can be used. The antibody or the fragment thereof in the kit of the present invention may be monoclonal or polyclonal. A fragment of the antibody is a part of the antibody (partial fragment) or a peptide containing a part of the antibody that retains the binding activity to the antigen of the antibody. The fragment of an antibody may include F(ab')$_2$, Fab', Fab, single chain Fv (scFv), disulfide-bonded Fv (dsFv) or a polymer thereof, a dimerized V region (Diabody), or a peptide containing CDR. As used herein, CDR is defined by Kabat et al., "Sequences of Proteins of Immunological Interest", U.S. Department of Health and Human Services, 1983, or Chothia et al., J. Mol. Biol., 196, 901-917, 1987. The kit of the present invention may include isolated nucleic acid encoding the antibody included in the kit of the present invention or encoding an amino acid sequence of fragment of the antibody, a vector including the nucleic acid, and a cell carrying the vector.

An antibody used for a kit of the present invention for predicting prognosis of cancer patient can be obtained by a method described above. Also, Binding of a label to an antibody or its fragment can be performed by a method as shown above. In addition, a commercially available labeling kit such as listed above may be used for labeling. The labeled antibody or its fragment can be detected by using an adequate instrument for proper labeling.

As a sample of the kit for predicting prognosis of cancer patient, tissue sample or fluid obtained from a subject for a biopsy can be used, for example. The sample is not particularly limited as long as it is adequate for immunological determination of the present invention, and may include tissue, blood, plasma, serum, lymph fluid, urine, serous fluid, spinal fluid, synovial fluid, aqueous humor, lacrimal fluid, saliva, or their fraction or treated sample. Preferably, sample for the kit is tissue, especially cancer tissue. Analysis can be performed qualitatively, quantitatively, or semi-quantitatively. In the above methods of the present invention for predicting prognosis of cancer patient, a cancer type of interest is not particularly limited and preferably is a solid cancer, such as lung cancer, head and neck cancer, esophageal cancer, cervical cancer, biliary cancer, breast cancer, and malignant melanoma.

C. Screening of Cancer Drug

In the other aspect, the present invention is directed to a method for screening cancer drug. Since DNA or RNA coding mutated NRF2 or mutated NRF2 protein may be used as an indicator of a prognosis of cancer patient, DNA or RNA coding mutated NRF2 or mutated NRF2 protein may also be used in screening of a cancer drug as an indicator for improved prognosis of a patient. For example, effect of the cancer drug to improvement of cancer prognosis can be determined by measuring the level of DNA or RNA coding mutated NRF2 or mutated NRF2 protein at a certain period of time after adding a test drug to a cancer cell or after administration of a test drug to a cancer model animal. More specifically, when a level of DNA or RNA coding mutated NRF2 or mutated NRF2 protein is decreased or not observed after addition or administration of a test drug, that drag can be selected as a treatment drug that improves cancer prognosis.

D. Cancer Drug

In the other aspect, the present invention is directed to a cancer drug that contains NRF2 inhibitor as an active ingredient. As used herein, a "NRF2 inhibitor" is not limited as long as it inhibits function or expression of NRF2 protein or expression of NRF2 gene, and may include such as, an antisense, dsRNA, a ribozyme, an aptamer, a fragment of a NRF2-binding protein, NRF2 antibody or its fragment, or binding protein.

An "antisense" refers to nucleic acid containing a sequence complementary to mRNA that encodes NRF2. The antisense may be consisted of DNA, RNA or both. The antisense does not need to be 100% complementary to mRNA of target NRF2. As long as it is able to specifically hybridize under stringent conditions (Sambrook et al. 1989), the antisense may contain non-complementary base. When the antisense is introduced into a cell, it binds to a target polynucleotide and inhibits transcription, RNA processing, translation or stability. The antisense includes, in addition to an antisense polynucleotide, polynucleotide mimetics, one containing modified back bone, and 3' and 5' terminal portions. Such antisense can be properly designed from NRF2 sequence information and produced using a method that is well known to those skilled in the art (for example, chemical synthesis).

A "dsRNA", refers to RNA containing double stranded RNA structure that inhibits gene expression by RNA interference (RNAi), and includes siRNA (short interfering RNA) and shRNA (short hairpin RNA). The dsRNA does not need to have a 100% homology to a target gene sequence so far as it inhibits expression of the target gene. A part of the dsRNA may be substituted with DNA for stabilization or other purpose(s). Preferably, the siRNA is double stranded RNA of 21 to 23 bases. The siRNA can be prepared by a method which is well known to those skilled in the art, for example, by chemical synthesis or as an analog of naturally occurring RNA. An shRNA is a short chain of RNA that has a hairpin turn structure. The shRNA can be prepared by a method that is well known to those skilled in the art, for example, by chemical synthesis or by introducing a DNA encoding shRNA into a cell and expressing the DNA.

A "ribozyme" is RNA possessing catalytic activity, and it is capable of cleaving, pasting, inserting, and transferring RNA. A structure of a ribozyme may be included hammerhead, hairpin, etc.

An "aptamer" is nucleic acids that bind to substance, such as protein. An aptamer may be RNA or DNA. The form of nucleic acids may be double stranded or single stranded. The length of an aptamer is not limited as far as it is able to specifically bind to a target molecule, and may be consisted of, for example, 10 to 200 nucleotides, preferably 10 to 100 nucleotides, more preferably 15 to 80 nucleotides, and further more preferably 15 to 50 nucleotides. An aptamer can be selected using a method that is well known to those skilled in the art. For example, SELEX (Systematic Evolution of Ligands by Exponential Enrichment) (Tuerk, C. and Gold, L., 1990, Science, 249, 505-510) may be employed.

A "fragment of a NRF2-binding protein" is a fragment of protein which binds to NRF2 and inhibits NRF2 to perform an original function. A NRF2 binding protein may include, for example, ferritin, light polypeptide (FTL), jun oncogene (JUN), cathepsin L1 (CTSL1), interleukin enhancer binding factor 3 (ILF3), KEAP1, pleckstrin homology domain interacting protein (PHIP), nuclear factor erythroid-derived 2 (NFE2), v-maf musculoaponeurotic fibrosarcoma oncogene homolog G (MAFG), and V-maf musculoaponeurotic fibrosarcoma oncogene family, protein K (MAFK). For example, a fragment of a NRF2-binding protein can be obtained by preparing partial peptide of such protein and selecting peptide that binds to NRF2. In addition, in order to improve its stability or enhance its inhibitory activity, the peptide may be properly modified, and an amino acid mutation may be introduced into a part of the peptide.

The number of amino acid that is recognized by anti-NRF2 antibody or its fragment used in a kit or treatment drug of the present invention is not particularly limited as long as the antibody is able to bind to NRF2. When an antibody is used as a treatment drug, it is preferable to recognize amino acid as many as it is able to inhibit the function of NRF2. The number of the amino acid that an antibody or its fragment recognizes is at least one and more preferably at least three. An immunoglobulin class of the antibody is not limited, and may be either IgG, IgM, IgA, IgE, IgD, or IgY, and is preferably IgG. The antibody of the present application may include any antibody isotypes.

As used herein, "fragment of an antibody" is a part of the antibody (partial fragment) or a peptide containing a part of the antibody retaining an activity for an antigen of the antibody. A fragment of antibody may includes $F(ab')_2$, Fab', Fab, single chain Fv (hereinafter, abbreviated as "scFv"), disulfide bonded Fv (hereinafter, abbreviated as "dsFv") or a polymer thereof, a dimerized V region (hereinafter, abbreviated as "Diabody"), or a peptide containing CDR.

$F(ab')_2$ is a fragment obtained by processing IgG with proteolytic enzyme pepsin as an antibody fragment of a molecular weight of about 100,000 with antigen avidity. A Fab' is an antibody fragment produced by cleavage of disulfide bonds on hinge region of the F(ab'), and it has a molecular weight of about 50,000 and antigen avidity. An sdFv is a polypeptide in which one VH and one VL are joined with a peptide linker, and it has antigen avidity. A dsFv is a fragment having antigen avidity in which amino acid residues substituted with cystein in VH and VL are joined via a disulfide bond. A Diabody is a fragment of dimerized scFvs. The Diabody of the present invention may be monospecific or bispecific (multispecific antibody). The dimerized scFv may be identical or different. A peptide containing CDR is a peptide containing at least one CDR amino acid sequence selected from CDR1, CDR2, and CDR3 of variable region of a heavy chain and CDR1, CDR2, and CDR3 of variable region of a light chain.

An antibody of the present invention can be produced by immunizing a nonhuman mammal or a bird with a peptide containing NRF2 or a part of NRF2, using an adjuvant(for example, a mineral oil or an aluminum precipitation and heat-killed bacterium or lipopolysaccharide, Freund's complete adjuvant, Freund's incomplete adjuvant, etc.) as necessary.

A NRF2 used as an immunogen is not limited as long as it is mammalian NRF2, such as a mouse, a rabbit, and a human, and is preferably human NRF2. An immunogen used for preparation of the antibody of the present invention can be obtained by introducing an expression vector containing cDNA encoding NRF2 into *Escherichia coli*, yeast, an insect cell, an animal cell, etc. and expressing it. When a peptide containing a part of NRF2 is used as an immunogen, it can be prepared by introducing an expression vector including cDNA which encodes such peptide into *Escherichia coli*, yeast, an insect cell, an animal cell, etc. and expressing it. When a peptide containing a part of NRF2 is used as an immunogen, a peptide containing a part of NRF2 or combined peptides in which one or more kind of parts of NRF2 is joined via a linker may be used.

A peptide containing NRF2 or a part of NRF2 can be produced by chemical synthesis using the Fmoc method, the Boc method, or the like. For example, a peptide that contains an desired amino acid sequence can be obtained by immobilizing C terminus amino acid of a peptide containing NRF2 or a part of NRF2 onto polystyrene resin, reacting an amino acid protected with a 9-fluorenylmethyloxycarbonyl group (Fmoc group) or a tert-butoxycarbonyl group (Boc group) using a condensing agent such as diisopropylcarbodiimide (DIC) to attach the deprotected amino acid to the C terminus amino acid, and repeating the process of wash and deprotection.

A peptide that contains NRF2 or a part of NRF2 can be also synthesized using an automated peptide synthesizer. Such a peptide synthesizer may include, for example, PSSM-8 (Shimazu Corporation), Model 433A Peptide Synthesizer (Applied Biosystems, Inc.), ACT 396 Apex (Advanced ChemTech Inc.), etc.

An animal to be immunized is not limited as long as a hybridoma can be produced, and such as a mouse, a rat, a hamster, a rabbit, a chicken and a duck, etc. can be used. Preferably a mouse or a rat, more preferably a mouse, and most preferably a NRF2 knockout mouse are used for immunization. An immunogen can be administered, for example, by a subcutaneous injection, an intraperitoneal injection, an intravenous injection, intradermal injection, an intramuscular injection, or a plantar injection, and preferably by a subcutaneous injection or an intraperitoneal injection. The amount of the immunogen is not limited as long as it is enough amount to produce an antibody, and preferably 0.1 to 1000 microgram, more preferably 1 to 500 microgram and further more preferably 10 to 100 microgram. An immunization can be performed once or several times with an adequate interval. The immunization is preferably performed 2 to 5 times with 1 to 5 weeks interval and more preferably performed 3 times with 3 weeks interval. One to two weeks after the last immunization, blood sample is collected from eye socket or caudal vein of an immunized animal, and antibody titer is measured using its serum. Measurement of antibody titer can be performed by a method that is well known to those skilled in the art, for example, radioisotope immunoassay (RIA), solid-phase enzyme-linked immunosorbent assay (ELISA), fluorescent antibody technique, and passive hemagglutination assay, and preferably performed by ELISA. An antibody of the present invention can be obtained by purification from the serum of an animal which shows a sufficient antibody titer.

A monoclonal antibody of the present invention can be produced by culturing a hybridoma that is obtained by fusing a myeloma cell with an antibody producing cell obtained from an animal that is immunized following the above mentioned method. Such the fusion method may be, for example, the method of Milstein et al. (Galfre, G. & Milstein, C., Methods Enzymol. 73:3-46, 1981). The antibody producing cell to be used can be collected from spleen, pancreas, lymph node, and peripheral blood, preferably spleen, of a mouse or a rat that has been immunized with the above-mentioned method and showed sufficient antibody titer in serum. A myeloma cell to be used is not limited as long as a cell is derived from a mammal, such as a mouse, a rat, a guinea pig, a hamster, a rabbit, or a human, and can be proliferated in vitro. Such a cell may include, for example, P3-X63Ag8 (X63) (Nature, 256, 495, 1975), P3/NS1/1-Ag4-1 (NS1) (Eur. J. Immunol., 6, 292, 1976), P3X63Ag8U1 (P3U1) (Curr. Top. Microbiol. Immunol., 81, 1, 1978), P3X63Ag8.653 (653) (J. Immunol., 123, 1548, 1979), Sp2/0-Ag14 (Sp2/O) (Nature, 276, 269, 1978), Sp2/O/FO-2 (FO-2) (J. Immunol. Methods, 35, 1, 1980), and is preferably P3U1.

The antibody producing cell and myeloma cell obtained by following the above mentioned method are washed with a medium, PBS (Phosphate Buffered Saline), etc., and then fused by adding cell agglutination medium, such as a polyethylene glycol (hereinafter, abbreviated as "PEG") (Elsevier Publishing, 1988). The ratios of the antibody producing cells and the myeloma cells to be fused may be in a range from 2:1 to 1:2, for example. After cell fusion has been performed, hybridoma is cultured in culture medium, such as HAT (hypoxanthine-aminopterin-thymidine) medium to allow selective proliferation. After the culture, culture supernatant is collected, and a sample that binds to an antigen protein, but does not bind to a non-antigen protein is selected by ELISA, etc. The sample is single-celled by the limiting dilution method, and a cell that stably shows high antibody titer is selected.

A monoclonal antibody can be obtained by culturing the hybridoma obtained by the abovementioned method in vitro followed by purification of the culture. Alternatively, the monoclonal antibody of the present invention can be obtained by preparing ascites after transplanting a hybridoma to an isogenic animal or an immunodeficiency animal to which pristane is previously administered into the abdominal cavity, and then purifying the collected ascites. Purification of a monoclonal antibody can be achieved, after centrifugal separation, by collecting IgG fractions using a protein A column, a protein G column, etc. When the antibody class is IgY and IgM, purification can be carried out on a column using mercaptopyridine as a ligand. Purification can be carried out, regardless of antibody class, using a NRF2 immobilized column, ion exchange chromatography, hydrophobic interaction chromatography, etc.

When an antibody is used as a treatment drug, it is preferable to use a humanized chimeric antibody, a humanized antibody or a human antibody as the antibody. A humanized chimeric antibody can be obtained by constructing DNA encoding VH and VL of a nonhuman animal-derived monoclonal antibody that binds to NRF2 to inhibit the function of NRF2, incorporating the constructed DNA into cDNA of constant region of a human-derived immunoglobulin and introducing the incorporated DNA into an expression vector, and introducing the vector into an adequate host cell to express it (Morrison, S. L. et al., Proc. Natl. Acad. Sci. USA, 81, 6851-6855, 1984).

A humanized antibody can be obtained by constructing DNA encoding V region in which an amino acid sequence that encodes CDR of VH and VL of a nonhuman animal-derived monoclonal antibody that binds to NRF2 to inhibit the function of NRF2 is transplanted into FRs of VH and VL of a human antibody, incorporating the constructed DNA into cDNA of constant region of a human-derived immunoglobulin and introducing the incorporated DNA into an expression vector, and introducing the vector into an adequate host cell to express it (see L. Rieohmann et al., Nature, 332, 323, 1988; Kettleborough, C. A. et al., Protein Eng., 4, 773-783, 1991; Clark M., Immunol. Today., 21, 397-402, 2000).

A human antibody can be obtained by using a human antibody phage library or a human antibody producing transgenic mouse, for example (Tomizuka et al., Nature Genet., 15, 146-156 (1997)). A human antibody phage library is a library of phages displaying Fab or scFv of a human antibody, etc. on the surface as a fusion protein by introducing VH gene and VL gene from an antibody gene-pool consisting of various sequences derived from human B cells, into a phage gene. Such a human antibody phage library may include a naive (non-immune) library, which is created by amplifying VH gene and VL gene of an antibody in a normal human from a peripheral blood lymphocyte, etc. using RT-PCR and generating a library thereof, (Cambridge Antibody Technology; Medical Research Council; Dyax Corp., etc.), a synthesized library, which is created by selecting a specific functional antibody gene in a human B cell, substituting a part of antigen binding regions in a V gene fragment such as a CDR3 region, with an oligonucleotide encoding an adequate length of a randomized amino acid sequence, and generating a library thereof, (BioInvent International AB.; Crucell; and MorphoSys AG), and an immune library, which is created form lymphocytes of a patient of cancer, autoimmune disease or infectious disease, or a person who is vaccinated with an antigen of interest as a vaccine.

A fragment of an antibody, such as F(ab')$_2$, Fab', Fab, scFv, dsFv or a polymer thereof, Diabody, or a peptide containing CDR, can be produced by following manners. The F(ab')$_2$ fragment can be obtained as an antibody fragment with antigen avidity that has a molecular weight of approximately 100,000 by treating an IgG antibody of the present invention that binds to NRF2 with proteolytic enzyme pepsin, and cleaving at amino acid residue 234 of H chain. Alternatively, a F(ab')$_2$ fragment of the present invention can be obtained by linking Fab's, which will be described below, via a thioether bond or a disulfide bond. A Fab' fragment of the present invention can be obtained by treating F(ab')$_2$ which binds to NRF2 obtained by the above-mentioned manner, with a reducing agent dithiothreitol. Alternatively, the Fab' fragment of the present invention can be obtained by inserting DNA that encodes Fab' of an antibody that binds to NRF2 into an expression vector, introducing the vector into a host cell, and expressing it. A Fab fragment can be obtained as an antibody fragment with antigen avidity that has a molecular weight of approximately 50,000 in which about a half of the region in the N terminal side of H chain and the entire region of L chain are linked via a disulfide bond, by treating the antibody that binds to NRF2 with proteolytic enzyme papain and cleaving at amino acid residue 224 of H chain. In addition, the Fab fragment can be obtained by inserting DNA that encodes Fab of an antibody that binds to NRF2 into an expression vector, introducing the vector into a host cell, and expressing the DNA. A scFv can be obtained by constructing DNA that encodes scFv by acquiring cDNA that encodes VH and VL of a NRF2-binding antibody, inserting DNA that encodes a linker sequence between these cDNAs, inserting the DNA into an expression vector, introducing the vector into a host cell, and expressing the DNA. The length of a linker is not limited as far as the linker allows association between VH and VL, and is preferably 10 to 20 residues and more preferably 15 residues. A sequence of a linker is not limited as long as it does not inhibit the folding of polypeptide chains of two domains, VH and VL. The linker is preferably consisted of glycine and/or serine and more preferably of GGGGS (G: a glycine, S:serine) sequence or its repeated sequence. A dsFv can be obtained by substituting one amino acid residue in each of VH and VL with a cysteine residue by site specific mutation, and linking VH and VL via a disulfide bond between the cysteine residues. The amino acid to be substituted is not limitied as long as the amino acid residue does not affect the antigen binding on the basis of the conformation. Diabody can be obtained by constructing DNA encoding the above scFv so that an amino acid sequence of the linker may be 8 residues or less (preferably five residues), inserting the DNA into an expression vector, introducing the vector into a host cell, and expressing it. Bispecific Diabody can be obtained by combining DNA of VH and VL from two different types of scFvs. A peptide containing CDR can be obtained by constructing DNA including DNA which encodes an amino acid sequence of CDR of VH or VL of an antibody that binds to NRF2, inserting the DNA into an expression vector, introducing the vector into a host cell, and expressing it.

A drug of the present invention may be administered as a medical drug either alone or with other drug. As another drug which can be administered with a drug of the present invention is not limited as long as it does not impair the effect of a treatment or a preventive drug of the present invention, and preferably a drug for treatment or prevention of cancer can be included, for example, an alkylating agent, such as ifosfamide, cyclophosphamide, dacarbazine, temozolomide, nimustine, busulfan, procarbazine, melphalan, and ranimustine; an antimetabolite, such as, enocitabine, capecitabine, carmofur, cladribine, gemcitabine, cytarabine, cytarabine ocfosfate, tegafur, tegafur-uracil, tegafur gimeracil oteracil potassium, doxifluridine, hydroxycarbamide, fluorouracil, fludarabine, pemetrexed, pentostatin, mercaptopurine, and methotrexate; a plant alkaloid, such as irinotecan, etoposide, sobuzoxane, docetaxel, nogitecan, paclitaxel, vinorelbine, vindesine, and vinblastine; an anticancerous antibiotic, such as actinomycin D, aclarubicin, amrubicin, idarubicin, epirubicin, zinostatin stimalamer, daunorubicin, doxorubicin, pirarubicin, bleomycin, peplomycin, mitomycin C, and mitoxantrone; a platinum based drug, such as oxaliplatin, carboplatin, cisplatin, and nedaplatin; a hormone drug, such as anastrozole, exemestane, estramustine, ethinylestradiol, chlormadinone, goserelin, tamoxifen, dexamethasone, toremifene, bicalutamide, flutamide, prednisolone, fosfestrol, mitotane, methyl-testosterone, medroxyprogesterone, mepitiostane, leuprorelin, and letrozole; a biological response modifier, such as interferon alfa, interferon b, interferon g, interleukin, ubenimex, dried BCG, and lentinan; and a molecular target drug, such as imatinib, gefitinib, gemtuzumab ozogamicin, tamibarotene, trastuzumab, tretinoin, bortezomib, and rituximab, etc.

A formulation of a drug of the present invention is not limited as far as it can be administered to a patient, and preferably a formation for an injection. A formulation of a drug of the present invention may be included a liquid formulation or a freeze dried formulation, for example. A drug of the present invention can include injectable form, an additive, for example, a solubilizing agent, such as propylene glycol, and ethylenediamine, etc.; a buffering agent, such as phosphate; a tonicity agent, for example, sodium chloride and glycerin, a stabilizing agent, such as sulfite; a preserving agent, such as phenol; and a soothing agent, such as lidocaine, (see "Iyakuhin Tenkabutsu Jiten (Japanese Pharmaceutical Excipients Directory)", Yakuji Nippo limited and "Handbook of Pharmaceutical Excipients Fifth Edition" APhA Publications). When a drug of the present invention is used as an injectable form, an ampule, a vial, a prefilled syringe, a pen injector-cartridge, an intravenous bag, etc. may be used as a storage container.

An administration route of a drug of the present invention is not limited as long as it exert desired curative effect or preventive effect, and preferably intravascular administration. Specifically, it can be administered into a blood vessel, for example, intravenous or intra-coronary arterial. An administration method of a drug of the present invention may include an intravenous administration by injection or intravenous drip infusion, and an intramuscular administration by intramuscular injection. The drug of the present invention may be administered by single, continuous, or intermittent administration. For example, a drug of the present invention may be continuously administered for 1 minute to 2 weeks. A drug of the present invention is preferably administered continuously for 5 minutes to 1 hour, and more preferably it is administered continuously for 5 minutes to 15 minutes.

A dosage of a drug of the present invention is not limited as long as a desired curative effect or preventive effect is obtained, and can be properly determined in accordance with symptom, gender, age, etc. The dosage of a curative drug or a preventive drug of the present invention can be determined, using, for example, the curative effect or preventive effect for cancer as an indicator. The dosage of a curative drug or a preventive drug of the present invention is preferably 1 ng/kg to 10 mg/kg, more preferably 10 ng/kg to 1 mg/kg, further preferably 50 ng/kg to 500 microgram/kg, further more preferably 50 ng/kg to 100 microgram/kg, further more preferably 50 ng/kg to 50 microgram/kg, and most preferably 50 ng/kg to 5 microgram/kg.

Mode for The Invention

Detailed examples of the present invention are described below. However, the present invention is not in any way limited to the aspects described in the examples.

EXAMPLE 1

NRF2 Gene Mutation in Esophageal Cancer

After extracting DNA from a clinical sample of esophageal cancer (a specimen excised by surgery) and esophageal cancer cell lines (KYSE-50, KYSE-70, KYSE-180), NRF2 genes were amplified by PCR, and then the sequence was determined by sequencing analysis. The primers used and their sequences are shown in Table 1. After amplifying each exon by PCR, a sequencing reaction was carried out using the same primers, and the sequences were decoded with a full automatic capillary sequencer (ABI 3130). PCR conditions were 30 seconds at 94 degrees C., 30 cycles of (30 seconds at 94 degrees C., 30 seconds at 55 degrees C., and 90 seconds at 72 degrees C.), and 5 minutes at 72 degrees C.

The positions of the mutations in the NRF2 gene and the amino acid substitutions caused in clinical samples of esophageal cancer and esophageal cancer cell lines (KYSE-50, KYSE-70, KYSE-180) are shown in FIG. 2. A mutation was detected in advanced cancer (18/82, 22%), and no mutation was detected in early cancer (0/36).

EXAMPLE 2

NRF2 Gene Expression in Normal Esophagus Epithelium and in Esophagus Cancer

NRF2 expression in normal esophagus (A and B) and in esophageal cancer (C) was detected by immunohistochemical staining using an antibody against NRF2. A specimen with a thickness of 3 micron was prepared from a sample of esophageal cancer that was formalin-fixed and paraffin-embedded, and it was reacted with a polyclonal anti-NRF2 antibody (C-20, Santa Cruz Biotechnology, diluted 100-fold). Then the expression was visualized using an immunohistological approach (stained brown).

The result is shown in FIG. 3. In the figure, an arrow represents a cell with expression. FIG. 3B is an enlarged view of a part of FIG. 3A. NRF2 expression confined to the bottom layer of basal cells was observed in the normal esophagus epithelium, and increased expression of NRF2 was observed in the esophageal cancer cell.

EXAMPLE 3

Correlation between NRF2 Gene Abnormality and a Vital Prognosis of a Cancer Patient Correlation between postoperative survival time and presence or absence of gene mutation was statistically analyzed (Kaplan-Meier analysis) for esophageal cancer cases where NRF2 gene mutation was screened.

TABLE 1

| Primers | Sequences | Sequence Id No. |
|---|---|---|
| NRF2-EX1 forward primer | 5' GCCGCCACCAGAGCCGCCCTGTC 3' | 3 |
| NRF2-EX1 forward primer (internal) | 5' AGCCCCAACACACGGTCCACAGCT 3' | 4 |
| NRF2-EX1 reverse primer | 5' GAAGCCGGTTGCGGCTGTCCCTC 3' | 5 |
| NRF2-EX2 forward primer | 5' ACCATCAACAGTGGCATAATGTG 3' | 6 |
| NRF2-EX2 reverse primer | 5' GGCAAAGCTGGAACTCAAATCCAG 3' | 7 |
| NRF2-EX3 forward primer | 5' TGAATATTTAGCTTGGCAATGTGA 3' | 8 |
| NRF2-EX3 reverse primer | 5' GGAGATTCATTGACGGGACTTAC 3' | 9 |
| NRF2-EX4 forward primer | 5' GTTTTGTAGTGGTGCCTTAGAGC 3' | 10 |
| NRF2-EX4 reverse primer | 5' TAATAGCACCCTCCAATCCTTCC 3' | 11 |
| NRF2-EX5-1 forward primer | 5' CTGAAGATAATGTGGGTAGGGAG 3' | 12 |
| NRF2-EX5-1 reverse primer | 5' TAGAAGTTCAGAGAGTGAATGGC 3' | 13 |
| NRF2-EX5-2 forward primer | 5' TCTGCTTTCATAGCTGAGCCCAG 3' | 14 |
| NRF2-EX5-2 reverse primer | 5' CAGGCAATTCTTTCTCTGGTGTG 3' | 15 |
| NRF2-EX5-3 forward primer | 5' ACCCTTGTCACCATCTCAGGGGC 3' | 16 |
| NRF2-EX5-3 reverse primer | 5' CATCTTCATCACGTAGCATGCTG 3' | 17 |
| NRF2-EX5-4 forward primer | 5' AAATGACAAAAGCCTTCACCTAC 3' | 18 |
| NRF2-EX5-4 reverse primer | 5' GCATTTCACATCACAGTAGGAGC 3' | 19 |

The result is shown in FIG. 4. There was a significant correlation between them with a statistic value of 0.005. A patient having cancer with an abnormality in NRF2 gene had poor vital prognosis compared to a patient having cancer without a NRF2 gene abnormality. This results suggest that a patient having an abnormality in NRF2 gene may need an active treatment after surgery.

EXAMPLE 4

A Growth-suppressive Effect on Cancer Cells due to dsRNA against NRF2

NRF2 gene expression was suppressed by dsRNA for the esophageal cancer cell lines that have NRF2 gene mutation (KYSE-50 and KYSE-180). Esophagus cancer cell lines were seeded into 96 well plates at 5000 cells/well, and control dsRNA (ON-TARGET plus Non-targeting Pool, Dharmacon, D-001810-10) or dsRNA against NRF2 (NRF2 dsRNA) (5'-UAAAGUGGCUGCUCAGAAUUU-3' (SEQ ID NO 20) and 5'-pAUUCUGAGCAGCCACUUUAUU-3' (SEQ ID NO 21)) were introduced using Lipofectamine (Lipofectamine RNAiMax, Invitrogen). Then they were incubated at 37 degrees C. for 72 hours. Then, the number of viable cells was determined by a MTS assay for the NADH activity (CellTiter 96 Aqueous One Solution Cell Proliferation Assay, Promega).

The result is shown in FIG. 5. In the figure, the ratio of cell counts for NRF2 dsRNA to cell counts for control dsRNA is shown. When NRF2 gene expression was suppressed by dsRNA in the esophageal cancer cell lines which have NRF2 gene mutation (KYSE-50 and KYSE-180), 26% (KYSE-50) or 38% (KYSE-180) of suppressive effect on proliferation was found compared with the control.

EXAMPLE 5

Identification of a Molecule Pathway Associated with NFR2 Activation by Biostatistical Analysis In order to investigate changes in gene expression due to NRF2 mutation, expression levels were compared between the genes expressed in the cells in which the mutated NRF2 gene was introduced and those expressed in the control cells, and a set of genes that were changed due to NRF2 mutation was analyzed. Two differently mutated NRF2 genes (NRF2-TK and NRF2-LF) were introduced into 293 cells, and clones that constantly express the mutated NRF2 were established. RNA was extracted from the established cells and the control cells (cells in which only a vector was introduced). After labeling 0.5 mg of total RNAs with Cy3-CPT, the expression levels were measured for approximately 30,000 genes using an Agilent gene expression microarray.

The gene expression in the two microarrays of NRF2 variants and the gene expression in the two microarrays of the control cells were compared using the IBMT method (Sartor M. A, Tomlinson C. R., Wesselkamper S. C., Sivaganesan S., Leikauf G. D., Medvedovic. Intensity-based hierarchical Bayes method improves testing for differentially expressed genes in microarray experiments. BMC Bioinformatics. 7:538-54, 2006). By the analysis, a p value that indicates the significant difference in expression between the genes was obtained. The obtained p value was corrected using Benjamini & Hochberg method (Benjamini, Y., and Hochberg, Y. (1995). Controlling the false discovery rate: a practical and powerful approach to multiple testing. Journal of the Royal Statistical Society Series B, 57, 289-300), and designated as a corrected p value. A gene having a p value of less than 0.05 was considered to be a statistically significant gene, and 2290 appropriate genes were obtained. In order to examine whether the 2290 genes were concentrated in a specific pathway, a statistical test based on hypergeometric distribution (Boyle, E.I., Weng, S., Gollub, J., Jin, H., Botstein, D., Chemy, J. M., Sherlock, G. (2004) GO: TermFinder-open source software for accessing Gene Ontology information and finding significantly enriched Gene Ontology terms associated with a list of genes, Bioinformatics 20, 3710-3715) was carried out against the gene set database published by BROAD institute (MsigDB, C2) (Subramanian A, Tamayo P, Mootha V K, Mukherjee S, Ebert B L, Gillette M A, Paulovich A, Pomeroy S L, Golub T R, Lander E S, Mesirov J P (2005). "Gene set enrichment analysis: a knowledge-based approach for interpreting genome-wide expression profiles". Proc. Natl. Acad. Sci. U.S.A. 102 (43): 15545-50). Then the obtained p value was corrected by the Benjamini & Hochberg method, which is mentioned above. A gene set having a p value of less than 0.05 was considered to be a statistically significant gene set.

As a result, PENG_RAPAMYCIN_DN was found from the gene sets which were statistically significant. The p value of PENG_RAPAMYCIN_DN is shown in Table 2. Using a biostatistics technique, PENG_RAPAMYCIN_DN and others were identified as molecule pathways that were significantly activated by activation of NRF2 gene. PENG_RAPAMYCIN_DN is a molecule pathway where the expression is decreased when treated with rapamycin, which is an mTOR pathway inhibitor. In other words, it is a pathway that can serve as an indicator of activation of mTOR pathway (Peng et al., Mol. Cell. Biol. 2002 August; 22 (15): 5575-5584).

TABLE 2

| | PATHWAY | | | | | |
|---|---|---|---|---|---|---|
| | x | n | M | N | p value | corrected p value |
| PENG_RAPAMYCIN_DN | x: 48 | n: 1909 | M: 229 | N: 16510 | 2.88E−05 | 1.94E−03 |

EXAMPLE 6

Response of Cancer Cells having NRF2 Gene Abnormality to an mTOR Inhibitor (Rapamycin)

Suppression of proliferation by rapamycin treatment was examined for the esophageal cancer cell lines without NRF2 gene abnormality (KYSE-30, KYSE-140, KYSE-170, KYSE-270) and for the cell lines with NRF2 gene abnormality (KYSE-50, KYSE-70, KYSE-180). The 7 esophageal cancer cell lines were seeded onto 96 well plates at 5000 cells/well, and 0, 1, 5, and 10 nM of rapamycin were added. After incubated at 37 degrees C. for 72 hours, viable cells were counted based on the NADH activity (MTS assay, CellTiter 96 Aqueous One Solution Cell Proliferation Assay, Promega).

In addition, growth suppression effect of rapamycin treatment to the lung cancer cell lines without NRF2 gene abnormality (SQ-5, QG-56) or with NRF2 gene abnormality (LK-2, EBC-1) and to the head and neck cancer cell lines without NRF2 gene abnormality (HO-1-N-1, HSC2) or with NRF2 gene abnormality (HO-1-u-1) were also examined by similar method for the above esophageal cancer cell lines.

The result is shown in FIGS. 6, 7 and 8. The graph shows the change in a ratio of cell counts for each cell line at each of the concentrations, when 0 nM (no drug added) is set as 100%. As shown in FIG. 6, cell proliferation of esophageal cancer cell lines with NRF2 gene abnormality was significantly suppressed by rapamycin treatment (decreased down to about 70% of the control). Also, as shown in FIGS. 7 and 8, cell proliferation of lung cancer cell lines and head and neck cancer cell lines with NRF2 gene abnormality was significantly suppressed by rapamycin treatment to about 62-70% and 70% of the control, respectively.

The entire contents of Japanese Patent Application No. 2008-192876 filed with the Japan Patent Office on Jul. 25, 2008, which serves as the basis for the priority claim of the present invention, are incorporated herein by reference.

Also, the entire contents of all patents, patent applications and reference documents cited in this application are incorporated herein by reference.

INDUSTRIAL APPLICABILITY

The efficacy prediction method in accordance with the present invention can be used as a method for predicting the response of a cancer patient to an mTOR-related cancer drug or predicting whether an mTOR-related cancer drug is effective for the cancer patient before administration. In addition, the prognostic prediction method in accordance with the present invention is able to provide important information for developing a therapy regimen strategy for a cancer patient by predicting the patient's prognosis. Furthermore, the method of the present invention for inhibiting the NRF2 gene or NRF2 protein and the treatment drug of the present invention comprising a NRF2 gene or NRF2 protein inhibitor can be used as a treatment method or a treatment drug for cancer.

The invention claimed is:

1. A method to identify and treat cancer susceptible to treatment with an mTOR inhibitor or a PI3K inhibitor in a subject which method comprises:
   (a) preparing DNA from a cancer sample originated from the subject;
   (b) hybridizing DNA contained in the cancer sample with primers that amplify DNA that comprises a mutation in a sequence that encodes NRF2 protein but can not amplify DNA without said mutation, and amplifying DNA that comprises the mutation;
   (c) detecting the amplified DNA to determine the presence of DNA with the mutation; and
   wherein said DNA with the mutation encodes an NRF2 protein wherein
   tryptophan at position 24 of SEQ ID NO:2 is replaced with a different amino acid;
   glutamine at position 26 of SEQ ID NO:2 is replaced with a different amino acid;
   isoleucine at position 29 of SEQ ID NO:2 is replaced with a different amino acid;
   leucine at position 30 of SEQ ID NO:2 is replaced with a different amino acid;
   glycine at position 31 of SEQ ID NO:2 is replaced with a different amino acid;
   glutamine at position 75 of SEQ ID NO:2 is replaced with a different amino acid;
   aspartic acid at position 77 of SEQ ID NO:2 is replaced with a different amino acid;
   glutamic acid at position 79 of SEQ ID NO:2 is replaced with a different amino acid;
   threonine at position 80 of SEQ ID NO:2 is replaced with a different amino acid; or
   glutamic acid at position 82 of SEQ ID NO:2 is replaced with a different amino acid; and
   (d) administering to said subject whose cancer DNA comprises said mutation an mTOR inhibitor and/or a PI3K inhibitor.

2. The method of claim 1 wherein in said NRF2 protein
   tryptophan at position 24 of SEQ ID NO:2 is replaced by cysteine or lysine;
   glutamine at position 26 of SEQ ID NO:2 is replaced by glutamic acid;

isoleucine at position 28 of SEQ ID NO:2 is replaced by glycine;

leucine at position 30 of SEQ ID NO:2 is replaced by phenylalanine;

glycine at a position 31 of SEQ ID NO:2 is replaced by alanine;

glutamine at position 75 of SEQ ID NO:2 is replaced by histidine;

aspartic acid at position 77 of SEQ ID NO:2 is replaced by valine or glycine;

glutamic acid at position 79 of SEQ ID NO:2 is replaced by lysine;

threonine at position 80 of SEQ ID NO:2 is replaced by lysine or proline; or glutamic acid at position 82 of SEQ ID NO:2 is replaced by aspartic acid.

* * * * *

SEQUENCE LISTING

<160> NUMBER OF SEQ ID NOS: 21

<210> SEQ ID NO 1
<211> LENGTH: 1818
<212> TYPE: DNA
<213> ORGANISM: Homo sapiens

<400> SEQUENCE: 1

```
atgatggact tggagctgcc gccgccggga ctcccgtccc agcaggacat ggatttgatt      60
gacatacttt ggaggcaaga tatagatctt ggagtaagtc gagaagtatt tgacttcagt     120
cagcgacgga aagagtatga gctggaaaaa cagaaaaaac ttgaaaagga aagacaagaa     180
caactccaaa aggagcaaga gaaagccttt ttcgctcagt tacaactaga tgaagagaca     240
ggtgaatttc tcccaattca gccagcccag cacatccagt cagaaaccag tggatctgcc     300
aactactccc aggttgccca cattcccaaa tcagatgctt tgtactttga tgactgcatg     360
cagcttttgg cgcagacatt cccgtttgta gatgacaatg aggtttcttc ggctacgttt     420
cagtcacttg ttcctgatat tcccggtcac atcgagagcc cagtcttcat tgctactaat     480
caggctcagt cacctgaaac ttctgttgct caggtagccc ctgttgattt agacggtatg     540
caacaggaca ttgagcaagt ttgggaggag ctattatcca ttcctgagtt acagtgtctt     600
aatattgaaa atgacaagct ggttgagact accatggttc caagtccaga agccaaactg     660
acagaagttg acaattatca tttttactca tctataccct caatggaaaa agaagtaggt     720
aactgtagtc cacattttct taatgctttt gaggattcct tcagcagcat cctctccaca     780
gaagacccca accagttgac agtgaactca ttaaattcag atgccacagt caacacagat     840
tttggtgatg aatttattc tgctttcata gctgagccca gtatcagcaa cagcatgccc     900
tcacctgcta ctttaagcca ttcactctct gaacttctaa atgggcccat tgatgtttct     960
gatctatcac tttgcaaagc tttcaaccaa aaccaccctg aaagcacagc agaattcaat    1020
gattctgact ccggcatttc actaaacaca agtcccagtg tggcatcacc agaacactca    1080
gtggaatctt ccagctatgg agacacacta cttggcctca gtgattctga agtggaagag    1140
ctagatagtg cccctggaag tgtcaaacag aatggtccta aaaccagt acattcttct    1200 ggggatatgg tacaaccctt gtcaccatct caggggcaga gcactcacgt gcatgatgcc    1260
caatgtgaga acacaccaga gaaagaattg cctgtaagtc ctggtcatcg gaaaacccca    1320
```

```
ttcacaaaag acaaacattc aagccgcttg gaggctcatc tcacaagaga tgaacttagg    1380
gcaaaagctc tccatatccc attccctgta gaaaaaatca ttaacctccc tgttgttgac    1440
ttcaacgaaa tgatgtccaa agagcagttc aatgaagctc aacttgcatt aattcgggat    1500
atacgtagga ggggtaagaa taaagtggct gctcagaatt gcagaaaaag aaaactggaa    1560
aatatagtag aactagagca agatttagat catttgaaag atgaaaaaga aaaattgctc    1620
aaagaaaaag gagaaaatga caaaagcctt cacctactga aaaaacaact cagcacctta    1680
tatctcgaag ttttcagcat gctacgtgat gaagatggaa aaccttattc tcctagtgaa    1740
tactccctgc agcaaacaag agatggcaat gttttccttg ttcccaaaag taagaagcca    1800
gatgttaaga aaaactag                                                  1818
```

<210> SEQ ID NO 2
<211> LENGTH: 605
<212> TYPE: PRT
<213> ORGANISM: Homo sapiens

<400> SEQUENCE: 2

```
Met Met Asp Leu Glu Leu Pro Pro Gly Leu Pro Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Arg Lys Glu Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Phe Ala Gln Leu Gln Leu Asp Glu Glu Thr
65                  70                  75                  80

Gly Glu Phe Leu Pro Ile Gln Pro Ala Gln His Ile Gln Ser Glu Thr
                85                  90                  95

Ser Gly Ser Ala Asn Tyr Ser Gln Val Ala His Ile Pro Lys Ser Asp
            100                 105                 110

Ala Leu Tyr Phe Asp Asp Cys Met Gln Leu Leu Ala Gln Thr Phe Pro
        115                 120                 125

Phe Val Asp Asp Asn Glu Val Ser Ser Ala Thr Phe Gln Ser Leu Val
    130                 135                 140

Pro Asp Ile Pro Gly His Ile Glu Ser Pro Val Phe Ile Ala Thr Asn
145                 150                 155                 160

Gln Ala Gln Ser Pro Glu Thr Ser Val Ala Gln Val Ala Pro Val Asp
                165                 170                 175

Leu Asp Gly Met Gln Gln Asp Ile Glu Gln Val Trp Glu Glu Leu Leu
            180                 185                 190

Ser Ile Pro Glu Leu Gln Cys Leu Asn Ile Glu Asn Asp Lys Leu Val
        195                 200                 205

Glu Thr Thr Met Val Pro Ser Pro Glu Ala Lys Leu Thr Glu Val Asp
    210                 215                 220

Asn Tyr His Phe Tyr Ser Ser Ile Pro Ser Met Glu Lys Glu Val Gly
225                 230                 235                 240

Asn Cys Ser Pro His Phe Leu Asn Ala Phe Glu Asp Ser Phe Ser Ser
                245                 250                 255

Ile Leu Ser Thr Glu Asp Pro Asn Gln Leu Thr Val Asn Ser Leu Asn
            260                 265                 270

Ser Asp Ala Thr Val Asn Thr Asp Phe Gly Asp Glu Phe Tyr Ser Ala
```

275                 280                 285
Phe Ile Ala Glu Pro Ser Ile Ser Asn Ser Met Pro Ser Pro Ala Thr
    290                 295                 300

Leu Ser His Ser Leu Ser Glu Leu Leu Asn Gly Pro Ile Asp Val Ser
305                 310                 315                 320

Asp Leu Ser Leu Cys Lys Ala Phe Asn Gln Asn His Pro Glu Ser Thr
                325                 330                 335

Ala Glu Phe Asn Asp Ser Asp Ser Gly Ile Ser Leu Asn Thr Ser Pro
            340                 345                 350

Ser Val Ala Ser Pro Glu His Ser Val Glu Ser Ser Tyr Gly Asp
        355                 360                 365

Thr Leu Leu Gly Leu Ser Asp Ser Glu Val Glu Glu Leu Asp Ser Ala
    370                 375                 380

Pro Gly Ser Val Lys Gln Asn Gly Pro Lys Thr Pro Val His Ser Ser
385                 390                 395                 400

Gly Asp Met Val Gln Pro Leu Ser Pro Ser Gln Gly Gln Ser Thr His
                405                 410                 415

Val His Asp Ala Gln Cys Glu Asn Thr Pro Glu Lys Glu Leu Pro Val
            420                 425                 430

Ser Pro Gly His Arg Lys Thr Pro Phe Thr Lys Asp Lys His Ser Ser
        435                 440                 445

Arg Leu Glu Ala His Leu Thr Arg Asp Glu Leu Arg Ala Lys Ala Leu
450                 455                 460

His Ile Pro Phe Pro Val Glu Lys Ile Ile Asn Leu Pro Val Val Asp
465                 470                 475                 480

Phe Asn Glu Met Met Ser Lys Glu Gln Phe Asn Glu Ala Gln Leu Ala
                485                 490                 495

Leu Ile Arg Asp Ile Arg Arg Arg Gly Lys Asn Lys Val Ala Ala Gln
            500                 505                 510

Asn Cys Arg Lys Arg Lys Leu Glu Asn Ile Val Glu Leu Glu Gln Asp
        515                 520                 525

Leu Asp His Leu Lys Asp Glu Lys Glu Lys Leu Leu Lys Glu Lys Gly
    530                 535                 540

Glu Asn Asp Lys Ser Leu His Leu Leu Lys Lys Gln Leu Ser Thr Leu
545                 550                 555                 560

Tyr Leu Glu Val Phe Ser Met Leu Arg Asp Glu Asp Gly Lys Pro Tyr
                565                 570                 575

Ser Pro Ser Glu Tyr Ser Leu Gln Gln Thr Arg Asp Gly Asn Val Phe
            580                 585                 590

Leu Val Pro Lys Ser Lys Lys Pro Asp Val Lys Lys Asn
        595                 600                 605

<210> SEQ ID NO 3
<211> LENGTH: 23
<212> TYPE: DNA
<213> ORGANISM: Artificial
<220> FEATURE:
<223> OTHER INFORMATION: primer sequence

<400> SEQUENCE: 3
gccgccacca gagccgccct gtc                                         23

<210> SEQ ID NO 4
<211> LENGTH: 24
<212> TYPE: DNA
<213> ORGANISM: Artificial

```
<220> FEATURE:
<223> OTHER INFORMATION: primer sequence

<400> SEQUENCE: 4
agccccaaca cacggtccac agct                                          24

<210> SEQ ID NO 5
<211> LENGTH: 23
<212> TYPE: DNA
<213> ORGANISM: Artificial
<220> FEATURE:
<223> OTHER INFORMATION: primer sequence

<400> SEQUENCE: 5
gaagccggtt gcggctgtcc ctc                                           23

<210> SEQ ID NO 6
<211> LENGTH: 23
<212> TYPE: DNA
<213> ORGANISM: Artificial
<220> FEATURE:
<223> OTHER INFORMATION: primer sequence

<400> SEQUENCE: 6
accatcaaca gtggcataat gtg                                           23

<210> SEQ ID NO 7
<211> LENGTH: 24
<212> TYPE: DNA
<213> ORGANISM: Artificial
<220> FEATURE:
<223> OTHER INFORMATION: primer sequence

<400> SEQUENCE: 7
ggcaaagctg gaactcaaat ccag                                          24

<210> SEQ ID NO 8
<211> LENGTH: 24
<212> TYPE: DNA
<213> ORGANISM: Artificial
<220> FEATURE:
<223> OTHER INFORMATION: primer sequence

<400> SEQUENCE: 8
tgaatattta gcttggcaat gtga                                          24

<210> SEQ ID NO 9
<211> LENGTH: 23
<212> TYPE: DNA
<213> ORGANISM: Artificial
<220> FEATURE:
<223> OTHER INFORMATION: primer sequence

<400> SEQUENCE: 9
ggagattcat tgacgggact tac                                           23

<210> SEQ ID NO 10
<211> LENGTH: 23
<212> TYPE: DNA
<213> ORGANISM: Artificial
<220> FEATURE:
<223> OTHER INFORMATION: primer sequence

<400> SEQUENCE: 10
gttttgtagt ggtgccttag agc                                           23
```

```
<210> SEQ ID NO 11
<211> LENGTH: 23
<212> TYPE: DNA
<213> ORGANISM: Artificial
<220> FEATURE:
<223> OTHER INFORMATION: primer sequence

<400> SEQUENCE: 11
taatagcacc ctccaatcct tcc                                            23

<210> SEQ ID NO 12
<211> LENGTH: 23
<212> TYPE: DNA
<213> ORGANISM: Artificial
<220> FEATURE:
<223> OTHER INFORMATION: primer sequence

<400> SEQUENCE: 12
ctgaagataa tgtgggtagg gag                                            23

<210> SEQ ID NO 13
<211> LENGTH: 23
<212> TYPE: DNA
<213> ORGANISM: Artificial
<220> FEATURE:
<223> OTHER INFORMATION: primer sequence

<400> SEQUENCE: 13
tagaagttca gagagtgaat ggc                                            23

<210> SEQ ID NO 14
<211> LENGTH: 23
<212> TYPE: DNA
<213> ORGANISM: Artificial
<220> FEATURE:
<223> OTHER INFORMATION: primer sequence

<400> SEQUENCE: 14
tctgctttca tagctgagcc cag                                            23

<210> SEQ ID NO 15
<211> LENGTH: 23
<212> TYPE: DNA
<213> ORGANISM: Artificial
<220> FEATURE:
<223> OTHER INFORMATION: primer sequence

<400> SEQUENCE: 15
caggcaattc tttctctggt gtg                                            23

<210> SEQ ID NO 16
<211> LENGTH: 23
<212> TYPE: DNA
<213> ORGANISM: Artificial
<220> FEATURE:
<223> OTHER INFORMATION: primer sequence

<400> SEQUENCE: 16
acccttgtca ccatctcagg ggc                                            23

<210> SEQ ID NO 17
<211> LENGTH: 23
<212> TYPE: DNA
<213> ORGANISM: Artificial
<220> FEATURE:
<223> OTHER INFORMATION: primer sequence
```

```
<400> SEQUENCE: 17
catcttcatc acgtagcatg ctg                                              23

<210> SEQ ID NO 18
<211> LENGTH: 23
<212> TYPE: DNA
<213> ORGANISM: Artificial
<220> FEATURE:
<223> OTHER INFORMATION: primer sequence

<400> SEQUENCE: 18
aaatgacaaa agccttcacc tac                                              23

<210> SEQ ID NO 19
<211> LENGTH: 23
<212> TYPE: DNA
<213> ORGANISM: Artificial
<220> FEATURE:
<223> OTHER INFORMATION: primer sequence

<400> SEQUENCE: 19
gcatttcaca tcacagtagg agc                                              23

<210> SEQ ID NO 20
<211> LENGTH: 21
<212> TYPE: RNA
<213> ORGANISM: Artificial
<220> FEATURE:
<223> OTHER INFORMATION: siRNA sequence against NRF2

<400> SEQUENCE: 20
uaaaguggcu gcucagaauu u                                                21

<210> SEQ ID NO 21
<211> LENGTH: 21
<212> TYPE: RNA
<213> ORGANISM: Artificial
<220> FEATURE:
<223> OTHER INFORMATION: siRNA sequence against NRF2

<400> SEQUENCE: 21
auucugagca gccacuuuau u                                                21
```